United States Patent [19]

Virnig

[11] 4,100,163

[45] Jul. 11, 1978

[54] SUBSTITUTED 8-SULFONAMIDOQUINOLINES

[75] Inventor: Michael J. Virnig, Fridley, Minn.

[73] Assignee: General Mills Chemicals, Inc., Minneapolis, Minn.

[21] Appl. No.: 652,005

[22] Filed: Jan. 26, 1976

[51] Int. Cl.² .................................. C07D 215/40
[52] U.S. Cl. ....................... 260/283 SA; 152/182; 260/270 D; 260/288 R; 260/288 CE; 423/24
[58] Field of Search ................... 260/283 SA

[56] References Cited

U.S. PATENT DOCUMENTS

| | | |
|---|---|---|
| 3,268,538 | 8/1966 | Billman et al. ............ 260/283 SA |
| 3,337,555 | 8/1967 | Billman et al. ............ 260/283 SA |
| 3,637,711 | 1/1972 | Budde et al. .................... 423/24 |
| 3,637,729 | 1/1972 | Harrington et al. ....... 260/283 SA |
| 3,954,936 | 5/1976 | Shozda ........................... 423/139 |

OTHER PUBLICATIONS

Belcher et al., *New Methods of Analytical Chem.*, 2nd Ed., Reinhold Pub. Co., N.Y., 1964, pp. 254–256.
Story, *The Solvent Extraction of Metal Chelates*, Pergammon Press, London (1964) pp. 2, 3, 31–34.
Ritcey et al., *CIM Bull*, Feb. 1975, pp. 105, 107, 112.
Martell et al., *Chem. of the Metal Chelate Compounds*, 1952, pp. 451–453.

*Primary Examiner*—Donald G. Daus
*Assistant Examiner*—David E. Wheeler
*Attorney, Agent, or Firm*—Patrick J. Span; Gene O. Enockson

[57] ABSTRACT

Certain sulfonamidoquinolines and metal complexes thereof both of which are soluble in essentially water-immiscible organic solvents. The sulfonamidoquinolines have the structural formula

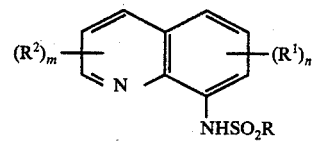

where the R, $R^1$ and $R^2$ groups and $m$ and $n$ are as defined in the specification and claims hereof. Solutions of the sulfonamidoquinolines and the metal complexes thereof in essentially water-immiscible organic solvents.

96 Claims, No Drawings

SUBSTITUTED 8-SULFONAMIDOQUINOLINES

The present invention relates to new sulfonamidoquinolines, organic solvent solutions thereof, metal complexes of such sulfonamidoquinolines and organic solvent solutions of such complexes.

Liquid ion exchange recovery of metal values from aqueous solutions thereof has in the past ten years or so become a mature commercial operation. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The main key to a successful application of liquid ion exchange is the reagent. In this respect, the reagent should meet a number of criteria. In the first instance, the reagent must complex with or react with a metal or group of metals and such complexing or reaction should be relatively fast in order to avoid having to use large holding tanks or reaction vessels. It is also desirable that the reagent shows preference for a single metal where the aqueous starting solutions contain a number of metal values. Such selectivity can often be optimized at designated pH ranges. The reagent should also desirably complex or react quantitatively with the metal under the extraction conditions. Additionally, the reagent, as well as the resulting metal complex, must exhibit satisfactory solubility in the essentially water-immiscible organic solvent being used. Further, the reagent-metal reaction or complexing must be reversible so that the metal can be stripped from the organic phase. For economic reasons, the reagent must be acceptably stable so that it can be recycled repeatedly. Also, it should be essentially water insoluble to prevent significant loss into the aqueous phase or phases. Furthermore, the reagent should not cause or stabilize emulsions. Again and principally for economic reasons, the reagent should not react with or load significant quantities of acid, for example, from aqueous acidic stripping solutions. And, of course, the cost of the reagent should be such that the liquid ion exchange process can be operated at a profit.

Of significant, but lesser, importance, is the selection of the essentially water-immiscible solvent to be used in the liquid ion exchange process. Such selection is important principally from a cost standpoint, especially in the recovery of the more common metals. Existing commercial operations for copper recovery, for example, generally employ aliphatic kerosenes because of the low cost thereof. Thus the cost of the reagent and the solvent is intertwined in providing the desired overall economics of the process being commercialized.

One of the most extensively used systems in commercial operation in the last decade for copper recovery has employed benzophenoximes or combination reagents including a benzophenoxime component. While being economic, improvements can be made since the said benzophenoximes do not have total selectivity for copper over iron, for example. Other types of reagents which have been proposed for use in copper recovery such as the alkenyl substituted 8-hydroxyquinolines also have certain drawbacks. Thus the latter compounds have poor selectivity for copper over iron and also tend to load considerable quantities of sulfuric acid.

I have now discovered certain sulfonamidoquinolines as more fully defined hereinbelow which are expected to find wide commercial use due to the fact that they generally meet most or all of the reagent characteristics set forth hereinabove, including low sulfuric acid loading and high selectivity for copper over iron. Further, most of my new sulfonamidoquinolines exhibit acceptable solubility in aliphatic and/or aromatic kerosenes thereby promoting their commercial use in economic liquid ion exchange processes. Additionally, they appear to have long term stability when in use equal to or greater than the aforementioned benzophenoximes. Other features and advantages of my invention will become apparent from the further descriptions hereinbelow.

In the making of my initial discovery of certain of the sulfonamidoquinolines of the invention, I was not aware of the work of Billman and Chernin relating to the precipitation of certain metal ions by chelating the same with selected low molecular weight sulfonamidoquinolines. This work is believed to have been first reported in Analytical Chemistry, Vol. 34, No. 3, March 1962, pp. 408–410. Such article shows the following four specific compounds.

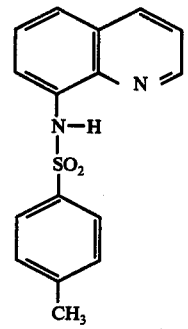
(1)

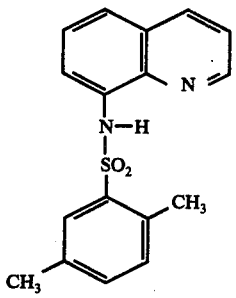
(2)

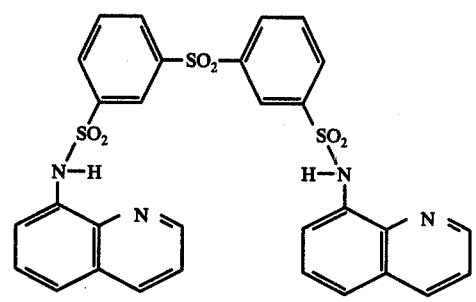
(3)

-continued (4)

These compounds were shown to chelate with $Ag^+$, $Cu^{+2}$, $Zn^{+2}$, $Pb^{+2}$, $Co^{+2}$ and $Hg^{+2}$ when dissolved in 95% ethanol or acetone and contacted with certain buffered solutions of the metal ions. The authors stated that "The chelates differ greatly from those of 8-quinolinol and 8-mercaptoquinoline in their solubility. They do not dissolve in the common nonpolar organic solvents or in the polar ones such as dimethylformamide, pyridine and nitromethane" (p. 408). Subsequently, U.S. Pat. Nos. 3,268,538 and 3,337,555 were issued to Billman and Chernin. No additional specific compounds are disclosed in these patents and the same are drawn to essentially the same data and concept as set forth in the earlier publication—i.e. the precipitation of chelates of specified metals with low molecular weight sulfonamidoquinolines. A generic formula

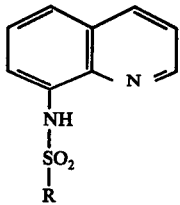

is set forth in the said patents with R being defined as a member of the group consisting of $C_1$–$C_5$ alkyl, $C_2$–$C_5$ alkenyl and

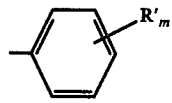

where m is a number from 0–2, R' is $C_1$–$C_5$ alkyl, $C_1$–$C_5$ alkyloxy, nitro, halo and

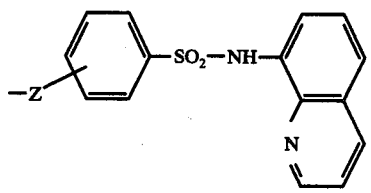

and Z is oxygen, sulfur, sulfonyl or sulfoxide.

The work of Billman and Chernin teaches away from the present invention in their findings of lack of solubility of the chelates of the low molecular weight compounds specifically synthesized and tested. Further, it cannot be seen how the formation of precipitates could lead to a commercially practical metal recovery process due to handling and cost problems.

I have discovered new sulfonamidoquinolines having properties making them useful in liquid ion exchange metal recovery processes. The new compounds of the present invention have the following structural formula:

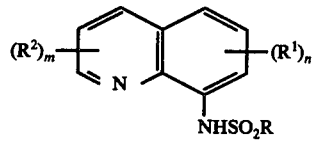

where R is alkyl, alkenyl, aralkyl, alkaryl or alkenylaryl (the terms "ar" and "aryl" as used herein include both unsaturated and saturated ring structures) as will be further defined. When alkyl or alkenyl, R will contain at least 5 carbon atoms and preferably 8 or more carbon atoms. The said alkyl or alkenyl groups also desirably contain less than about 20 carbon atoms and additionally are preferably branched chain. R is, however, preferably aralkyl, alkaryl or alkenylaryl as represented by

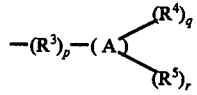

where p is 0 or 1 and when p is 1, $R^3$ is an alkylene radical of 1 to about 20 carbon atoms, preferably 1 or 2 carbon atoms. "A" is a mono or polycyclic radical wherein the ring or rings are 5 or 6 membered. While the said mono or polycyclic radical may be saturated or unsaturated, it is preferred that the same is unsaturated and 6 membered and A is most preferably selected from the phenyl and naphthyl radicals. In these aralkyl, alkaryl and alkenylaryl compounds, q is a whole integer of preferably 1–5 and $R^4$ is an alkyl or alkenyl group such that the total number of carbon atoms in $(R^4)_q$ is at least five with the provisos that when q is 2 at least one $R^4$ radical contains 5 or more carbon atoms and when q is 3 or more at least one $R^4$ radical contains 3 or more carbon atoms. Preferably, the total number of carbon atoms in $(R^4)_q$ is eight or more. Additionally, the $R^4$ groups are preferably alkyl and q is most preferably 1, 2 or 3. The $R^4$ groups may individually contain 20 or more carbon atoms but there is no particular advantage in groups of more than 20 carbon atoms since the same would tend to increase overall molecular weight of the sulfonamidoquinolines without any consequent increase in extraction capabilities. In my preferred aralkyl, alkaryl and alkenylaryl compounds, r is 0, 1 or 2 and $R^5$ is Cl, Br, nitro or —O—$R^6$ where $R^6$ is a hydrocarbon group such as alkyl, alkenyl, aryl, aralkyl, alkaryl or alkenylaryl containing from 1 to about 20 carbon atoms. It is preferred that r is 0 or 1. When A is phenyl, q + r is 5 or less.

$R^1$ and $R^2$ in the new compounds of the present invention can be hydrocarbon groups such as alkyl, alkenyl, aryl, aralkyl, alkaryl or alkenylaryl containing from 1 to about 20 carbon atoms, ether groups, —O—$R^6$, as defined hereinabove or Cl, Br or nitro groups. In respect thereto, n and m are 0, 1, 2 or 3. Preferably, when present, $R^1$ and $R^2$ are alkyl groups of 1 to 5 carbon atoms or Cl, Br or nitro groups. Preferred compounds of the invention are those wherein m and n are 0 or 1. When m or n are 2 and $R^2$ or $R^1$ are aliphatic hydrocarbon groups, the two such hydrocarbon groups can form an additional condensed ring system on the basic quinoline nucleus.

The compounds of the present invention also preferably contain less than about 30 carbon atoms in the R radical thereof. They are also characterized as having solubilities in essentially water-immiscible organic solvents of at least 2% by weight. Correspondingly, they are also further characterized in that the copper ($Cu^{++}$) complexes of the compounds have solubilities of at least 2% by weight in the said essentially water-immiscible organic solvents. Especially preferred compounds of the invention are characterized by their solubility (and the $Cu^{++}$ complexes thereof) in aliphatic or aromatic hydrocarbons or mixtures thereof having flash points of 150° F. and higher to the indicated level of at least 2% by weight.

As will be further evident from the Examples to follow, alkyl and alkenyl chain length and/or branching and type of branching in the R radical (including in the aralkyl, alkaryl and alkenylaryl compounds) can contribute to the solubilities as above set forth. Thus the compounds of the invention may preferably even be further characterized as having in the R radical sufficient chain length and/or branching and type of branching in the alkyl and alkenyl groups contained therein to provide at least the minimum solubility characteristics as set forth in the respective solvents to be used. In this latter respect, it was discovered that in order for the compounds (and their $Cu^{++}$ complexes) to meet the solubility requirements in the above designated aliphatic and/or aromatic solvents having flash points of 150° F. and higher, the same have 8 or more carbon atoms in R when R is alkyl or alkenyl and, when R is

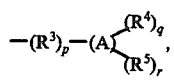

$(R^4)_q$ contains 8 or more carbon atoms with the proviso that when $q$ is 2 and one $R^4$ radical contains five carbon atoms, the second $R^4$ radical will also contain at least five carbon atoms.

The new compounds of the present invention are preferably prepared by first dissolving 8-aminoquinoline or a substituted 8-aminoquinoline in an organic base or a solution of an organic base in an organic solvent. Such solution is cooled to 0°–10° C. and the desired sulfonyl chloride is added slowly with stirring while the reaction temperature is maintained at 0° to 20° C. After addition of the sulfonyl chloride is complete, the reaction mixture is allowed to warm to room temperature, preferably with stirring for 1 to 3 hours for example. The reaction mixture is then heated to 80°–100° C. for approximately 30 minutes. Water is added and the reaction mixture (at 75°–95° C. for example) is stirred for an additional period—i.e. 30 minutes. The reaction mixture is then poured into water (ratio of 250 ml. to 1 liter) and the sulfonamidoquinoline is recovered (1) by extraction with an organic solvent, such as Skellysolve C (available from the Skelly Oil Co. and consists mostly of n-heptane, b.p. range 88°–100° C., hereinafter referred to as "Skelly C"), benzene, chloroform and the like or (2) by filtration in the case of those sulfonamidoquinolines which crystallize. After extraction, the organic extract is desirably washed (3 times) with 2–5% by weight sodium bicarbonate in 20–30% aqueous methanol, then with 25 g./l. aqueous sulfuric acid (3 times) and again with the sodium bicarbonate solution. Finally, the organic is washed with brine, dried over sodium sulfate, filtered and evaporated in vacuo. Further details of the synthesis of the compounds of the present invention will be found in the Examples to follow including information on the preparation of various of the starting materials.

As indicated, my new sulfonamidoquinolines find use in the recovery of metal values from their aqueous solutions. As such, they are the preferred compounds for use in the process disclosed and claimed in my copending application entitled Extraction Recovery Of Certain Metal Values, filed of even date with the present application. In said process, the compounds are dissolved in an essentially water-immiscible organic solvent and then the resulting solution is contacted with the metal containing aqueous phase to extract at least a portion of the metal values into the organic phase. The phases are separated and metal values are stripped from the loaded organic phase by the use of an aqueous stripping medium.

A wide variety of essentially water-immiscible organic solvents can be used in the said metal recovery process. These include: aliphatic and aromatic hydrocarbons such as kerosenes, benzene, toluene, xylene and the like. The choice of the said essentially water-immiscible organic solvent for particular commercial operations will depend on a number of factors including the design of the solvent extraction plant (i.e. mixer-settlers, Podbielniak extractors, etc.), the value of the metal being recovered, disposal of plant effluent and the like. The sulfonamidoquinolines of the present invention find particular use in the extraction recovery of the major, non-ferrous, transition metals—i.e. copper, nickel, zinc, cobalt(II), cadmium, mercury and silver(I) . . . and lead as will be described more fully hereinbelow. Essentially all of the major plants in operation currently for the recovery of these metals (particularly $Cu^{++}$) use mixer-settlers with relatively large organic inventories and some loss of solvent invariably occurs by evaporation, entrainment in the aqueous, and the like. Under these circumstances, preferred organic solvents for use in the metal recovery processes are the aliphatic and aromatic hydrocarbons having flash points of 150° F. and higher and solubilities in water of less than 0.1% by weight. These solvents are also essentially non-toxic and chemically inert and the costs thereof are currently within practical ranges—i.e. normally less than 1 dollar (U.S.) per gallon to as low as 30¢ (U.S.) or so. Representative commercially available solvents are: Kermac 470B (an aliphatic kerosene available from Kerr-McGee—Flash Point 175° F.), Chevron Ion Exchange Solvent (available from Standard Oil of California—Flash Point 195° F.), Escaid 100 and 110 (available from Exxon-Europe—Flash Point of ≃180° F.), Norpar 12 (available from Exxon-U.S.A.—Flash Point 160° F.), Conoco C-1214 L (available from Conoco—Flash Point 160° F.), Aromatic 150 (an aromatic kerosene available from Exxon-U.S.A.—Flash Point 150° F.) and various other kerosenes and petroleum fractions available from other oil companies.

The present invention also relates to new compositions wherein the sulfonamidoquinolines of the invention are dissolved in the essentially water-immiscible organic solvents. In this respect, liquid ion exchange reagents are often sold as solutions in organic solvents. Thus the new compositions of the invention consist essentially of solutions of 2% by weight or more of the sulfonamidoquinolines in the essentially water-immiscible organic solvents. When sold as concentrates, the solutions will preferably contain from about 25 to 75% by weight of the sulfonamidoquinolines. In use in the liquid ion exchange metal recovery processes, the solutions will preferably contain from about 2 to 50% by weight of the sulfonamidoquinoline compounds and even more preferably from about 5 to 20% by weight thereof.

In the extraction processes using the new sulfonamidoquinolines of the present invention, the organic:aqueous phase ratios can vary widely since the contacting of any quantity of the sulfonamidoquinoline solution with the metal containing aqueous phase will result in extraction of metal values into the organic phase. However, for commercial practicality, the organic:aqueous phase ratios are preferably in the range of 5:1 to 1:5. For practical purposes, the extractions (and stripping) are normally carried out at ambient temperatures and pressures although higher or lower temperatures and/or pressures can be used. The entire process can be carried out continuously with the stripped organic solvent solution being recycled for contacting further quantities of metal containing solutions.

The metal recovery process using the new sulfonamidoquinolines of the present invention is useful for the recovery of the following metal values from their aqueous solutions: $Cu^{++}$, $Ni^{++}$, $Co^{++}$, $Zn^{++}$, $Pb^{++}$, $Cd^{++}$, $Hg^{++}$ and $Ag^{+}$. Except for $Pb^{++}$, these metal values are all transition metals of Groups I b, II b and VIII. The extraction of these various metals from their aqueous solutions depends upon a number of factors including, for example, the concentration of the metal ion, the particular anions present, and the pH and/or ammonia concentration in or of the aqueous solutions and the concentration of and the particular sulfonamidoquinoline used in the organic phase. Thus for each aqueous metal solution and reagent solution of sulfonamidoquinoline there will be a preferred or optimum set of extraction conditions, and those skilled in the art, based on the information given herein especially in respect of the examples to follow, will be able with a limited number of trial runs to determine such preferred or optimum conditions for the respective systems under consideration. This is equally true of the stripping operations. By stripping is meant that at least a portion of the metal values in the loaded organic phase are transferred to the aqueous stripping medium. The metal values are then desirably recovered from the aqueous stripping medium by conventional techniques, preferably electrolysis. The loaded organic:aqueous stripping phase ratios can also vary widely. However, the overall object of the process is to provide a metal containing stripping solution of known composition and concentration suitable for conventional recovery techniques such as electrolysis. Thus normally the metal will preferably be present in higher concentrations in the aqueous stripping medium than in the starting metal containing solution. Accordingly, the loaded organic:aqueous stripping medium phase ratio will preferably be in the range of 1:1 to 10:1.

Based upon extensive data obtained to date especially in respect of the new sulfonamidoquinolines of Examples I and II to follow, certain preferred conditions for the extraction and stripping operations are outlined as follows in regard to specific metal ions to be extracted. Thus $Cu^{++}$ is readily extracted at acid pH's with the preferred range falling at a pH of from about 0.5 to 7.0.

Likewise, copper is readily extracted from ammoniacal solutions wherein the preferred concentration of ammonia in the latter is from about 10 to 150 g./l. The loaded organic is readily stripped of $Cu^{++}$ with aqueous acidic stripping solutions such as 25 to 250 g./l. $H_2SO_4$.

Zinc ($Zn^{++}$), nickel ($Ni^{++}$), cobalt ($Co^{++}$) and cadmium ($Cd^{++}$) are readily extracted from ammoniacal solutions in the same manner as $Cu^{++}$. Preferred acid pH ranges for these metals are about 4.0 to 6.0 for $Zn^{++}$, about 4.5 to 7.0 for $Ni^{++}$, about 5.0 to 7.0 for $Co^{++}$ and about 4.0 to 7.0 for $Cd^{++}$. All of these metals are readily stripped from the loaded organic phases thereof with aqueous acidic stripping mediums, preferably 25 to 250 g./l. $H_2SO_4$. Lead ($Pb^{++}$) is preferably extracted at pH's above about 5.0 with the metal being stripped from the loaded organic by aqueous acidic stripping solutions, which are preferably about 100 to 150 g./l. nitric acid solutions (lead has little solubility in aqueous $H_2SO_4$). $Pb^{++}$ does not form a soluble ammonia complex. Mercury ($Hg^{++}$) is (from somewhat limited data) preferably extracted from its aqueous solutions over a pH range of about 0.5 to 6.0. One preferred aqueous acidic stripping medium therefore is hydrochloric acid at a concentration of about 20 to 50 g./l. Silver ($Ag^{+1}$) was extracted from an ammoniacal solution, specifically at an ammonia concentration of 10 g./l. Specific aqueous stripping solutions for the silver loaded organic were 63 g./l. nitric acid, 37 g./l. HCl and 150 g./l. $H_2SO_4$. The above discussion is based on actual extraction and stripping operations in accordance with the Procedures used in the Examples to follow. As indicated previously, each starting metal containing aqueous solution will have its own optimum conditions as will be readily apparent to those skilled in the art.

The present invention also relates to the metal complexes of the new sulfonamidoquinolines and to the essentially water-immiscible organic solvent solutions thereof. The latter consists essentially of the said solvent and 2% or more by weight therein of the metal complexes (preferably less than about 75% by weight), the metals being defined hereinabove in respect of the extraction process using the new sulfonamidoquinolines of the invention. While not normal practice in the industry, the solutions of the metal complexes can be obtained at one location and transferred to another for stripping as described. The term "metal complexes" as used herein is meant to include compositions of the new sulfonamidoquinolines with other than insignificant quantities of the metals as hereinabove defined combined therewith. The exact structural nature of these complexes has not been determined. However, from the analytical data obtained wherein the new sulfonamidoquinolines have been maximum loaded with the metals, particularly $Cu^{++}$ and $Zn^{++}$, it would appear that preferred metal complexes (i.e. maximum loaded) comprise the metal and the new sulfonamidoquinoline in a molar ratio of about 1:2. However, as indicated, the new sulfonamidoquinolines do not need to be maximum loaded to perform acceptably in liquid ion exchange processes and thus the metal complexes thereof are generally defined as including the designated metals in more than insignificant quantities up to maximum loading.

The starting materials for the preparation of the new sulfonamidoquinolines were prepared (if not readily available commercially) by various methods as will now be described in detail. Such description aids in defining preferred embodiments of the invention since branching of the alkyl or alkenyl groups in R and type of branching in

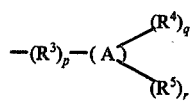

is dependent somewhat on the derivation of the starting materials.

Starting alkylbenzenes were prepared by two different routes. The first involved the acylation of a suitable aromatic substrate with an acid chloride followed by reduction to the alkylbenzene. This procedure was used in the preparation of diamylbenzene and n-hexadecylbenzene as will be more fully detailed hereinbelow with respect to preparation of the sulfonamidoquinoline compounds where R is diamylphenyl and n-hexadecylphenyl.

The second route to the starting alkylbenzenes involves a Friedel-Crafts alkylation of benzene or suitable alkylbenzene such as toluene or cumene. Essentially the alkylations were carried out via the procedure of Oleson (Ind. Eng. Chem., 52, 833 (1960)). More specifically, approximately one-half to two-thirds of the starting aromatic hydrocarbon and the aluminum chloride were placed in a round bottom three-neck flask fitted with mechanical stirrer, addition funnel, thermocouple well or thermometer, and a condenser. A small portion of water (2 to 10 drops) was added and then a solution of the olefin in the remainder of the aromatic hydrocarbon was added slowly with stirring to the reaction vessel. The reaction temperature was maintained in the range from 0° to 50° C. After addition was complete, the reaction mixture was stirred for an additional 15 to 20 minutes while the reaction temperature was maintive groups. The soft alkylate types are biodegradable whereas the hard alkylate types are not. The "soft alkylate" type can also be referred to as linear alkylates meaning that the alkyl group is attached to the benzene nucleus in a definite manner—i.e.

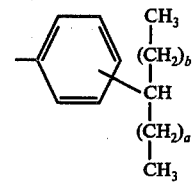

where $a$ and $b$ would be 0 or whole integers such as to complete the chain length of the alkyl group. For illustration purposes, the alkylation of benzene with 1-dodecene can theoretically yield a mixture of alkylbenzene isomers including the following:

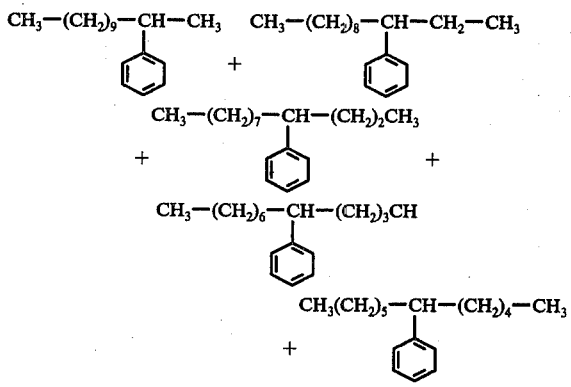

Table 1

| Product | Run | Aromatic Hydrocarbon | Olefin | AlCl$_3$ (moles) | Reaction Temp. °C | Boiling Point mm of Hg | Boiling Point °C | Yield % |
|---|---|---|---|---|---|---|---|---|
| Hexadecylbenzene | | Benzene 3.5m[1] | 1-Hexadecene 0.5m[1] | 0.025 | 50 | 0.45 | 140–155 | 56 |
| Decylmethylbenzene | A | Toluene 10m | 1-Decene 1m | 0.025 | 0–5 | [2] | 150–155 | 79.9 |
| | B | Toluene 71.4m | 1-Decene 7.6m | 0.357 | 40 | 0.55–0.8 | 106–124 | 76 |
| Decylethylbenzene | A | Ethylbenzene 5m | 1-Decene 1m | 0.025 | 40 | 0.3–0.5 | 121–125 | 55 |
| | B | Ethylbenzene 5m | 1-Decene 1m | 0.025 | 0–5 | [3] | 85–105 | 58 |
| Octylmethylbenzene | | Toluene 5m | 1-Octene 1.5m | 0.45 | 25 | 0.20 | 60–90 | 69 |
| C$_{11}$–C$_{14}$ Alkylmethylbenzene | | Toluene 5m | C$_{11}$–C$_{14}$ Chevron[4] α-olefin ~1m | 0.025 | 40–44 | 0.04 | 83–120 | 66 |
| Decylcumene | | Cumene 5m | 1-Decene 1m | 0.025 | 40 | 0.05 | 119–135 | 75 |
| Heptylbenzene | | Benzene 7m | 1-Heptene 1m | 0.05 | 50 | Atmos. | 227–233 | 69 |

[1]Amounts in moles
[2]Water aspirator vacuum
[3]Pressure was not recorded
[4]Available from Standard Oil of California and is further described as follows: A mixture of predominantly straight chain mono-olefins designated by the formula CH$_3$—(CH$_2$)$_n$—CH=CH$_2$, where n = 7 to 12, with an average molecular weight of 170–176.

tained as indicated. A 10% by weight aqueous hydrochloric acid solution (500 ml.) was added and the mixture stirred for five minutes. The phases were then separated and the organic phase was washed twice with 2-5% by weight aqueous sodium hydroxide, once with brine, and the excess aromatic was stripped off in vacuo. The product was fractionally distilled through a vigreaux column under vacuum. The ratios of reactants, boiling points and yields are found in Table I which follows hereinbelow. It is to be noted that this method yields alkylbenzenes of the so-called "soft alkylate" type which are preferred starting materials for the preparation of the alkaryl substituted sulfonamidoquinolines of the invention. The terms "soft" and "hard" alkylate are descriptive and are based on the biodegradability of the alkylbenzene sulfonic acids containing the respec- The starting sulfonyl chlorides were prepared by four different routes starting from the alkylbenzene, the alkylbenzenesulfonic acid, the sodium sulfonate salt or an alkyl halide. In the first of these methods, a solution of the alkylbenzene in 1,1,2-trichloroethane (TCE) was cooled to 10° C. and chlorosulfonic acid was added slowly with stirring. The pot temperature was maintained at 10°–15° C. during the addition. After the addition was complete, the reaction mixture was stirred at 10°–15° C. for 15 minutes and then allowed to warm to ambient temperature while stirring for 2-3 hours. Thionyl chloride was added to the stirring reaction mixture and the same was then heated slowly (1-3 hours) to 90°–120° C. and held at this temperature for 30 minutes. A sample was then withdrawn from the reaction mixture for analysis. If the presence of the sulfonic acid anhydride was detected by IR, an additional mole of thionyl chloride was added and the reaction mixture was stirred at 90°–120° C. for 1 additional hour. The excess thionyl chloride and TCE were stripped from the reaction mixture in vacuo and the crude sulfonyl chloride was purified by molecular distillation. Ratios of reactants, reaction temperatures and yields are given in Table 2:

Table 2

| Product | Run | Alkyl-benzene (m) | ClSO$_3$H (m) | SOCl$_2$ (m) | TCE (ml) | Rxn Temp. °C. | Distilled Yield (%) |
|---|---|---|---|---|---|---|---|
| Dodecylbenzenesulfonyl chloride | | 4.34 | 4.34 | 8.68 | 367 | 115–120 | 64 |
| Decylmethylbenzene-sulfonyl chloride | A | 5.53 | 5.53 | 11.07 | 442 | 110 | 73 |
| | B | 0.25 | 0.275 | 0.55 | 10 | 116 | 56 |
| Decylethylbenzene-sulfonyl chloride | A | 0.7 | 0.7 | 1.4 | 40 | 110 | 46 |
| | B | 0.56 | 0.56 | 1.13 | 33 | 110 | 41 |
| C$_{11}$–C$_{14}$ Alkylmethyl-benzene sulfonyl chloride | | 0.6 | 0.6 | 1.2 | 40 | 120 | 38[1] |
| Nonylmethylbenzene-sulfonyl chloride | | 0.25 | 0.275 | 0.55 | 30 | 110 | 84 |
| Decylcumenesulfonyl chloride | | 0.46 | 0.46 | 0.93 | 20 | 90 | 34[1] |
| Heptylbenzenesulfonyl chloride | | 0.67 | 0.67 | 1.0 | [2] | 120[3] | 50 |

[1]Repeated addition of thionyl chloride did not convert the sulfonic acid anhydride to the sulfonyl chloride quantitatively.
[2]TCE was replaced with 30 ml. of Skelly C
[3]Dimethylformamide (0.4 ml.) was added while holding the temperature at 120° C. to catalyze the conversion.

Octylmethylbenzenesulfonyl chloride was prepared from octyltoluene in 70% yield by the method of Cross and Chaddix (U.S. Pat. No. 2,694,727). Other of the starting sulfonyl chlorides were prepared by mixing the alkylbenzene with chlorosulfonic acid in the manner set forth by Bistline and coworkers (J. Am. Oil Chem. Soc., 51, 126 (1974)) and the reaction was carried out with the following modifications. The acid layer was drained off after the reaction mixture was allowed to stand overnight and Skelly C was added to the organic with gentle swirling. An additional volume of sulfuric acid settled out of the organic after one hour and was drained off. The organic was carefully washed with ice water (with extreme caution), then with brine, dried over sodium sulfate, filtered, and evaporated in vacuo to an oil. Ratios of reactants and solvents are given in Table 3.

Table 3

| Product | Alkyl-benzene (m) | ClSO$_3$H (m) | 1,2-Di-chloro-ethane (ml) | Skelly C (ml) | Yield % |
|---|---|---|---|---|---|
| Dodecylben-zenesulfonyl chloride | 0.615 | 1.45 | 100 | 500 | 80 |
| Diamylben-zenesulfonyl chloride | 0.224 | 0.67 | 25 | 100 | (1) |
| n-Hexadecyl-benzene-sulfonyl chloride | 0.33 | 1 | 50 | 100 | (2) |
| Hexadecylben-zenesulfonyl chloride | 0.2 | 0.6 | 50 | (3) | (2) |

(1) Approximately 40% of the material was lost during the ice water wash due to vigorous frothing and spattering. The crude product was purified by distillation (37% yield).
(2) The conversions were incomplete. The isolated material was a mixture of the sulfonic acid and sulfonyl chloride. Conversion to the sulfonyl chloride was completed by refluxing with excess thionyl chloride as described in the following procedure.
(3) Addition of the Skelly C was omitted.

In preparing the starting alkylbenzenesulfonyl chlorides, from the alkylbenzenesulfonic acids, the sulfonic acid was added slowly over a 4 hour period to a stirring solution of thionyl chloride (1 liter) in Skelly C (500 ml.). The temperature controller was set for 95° C. and the reaction mixture was heated to reflux. The reaction mixture required approximately 2 hours to reach 95° C. After stirring at 95° C. overnight, the excess thionyl chloride and the Skelly C were stripped off under aspirator vacuum. An additional 50 ml. of Skelly C was added and then distilled off under aspirator vacuum to remove the last traces of thionyl chloride. The crude product was then purified by molecular distillation. Amounts of starting acid and yields are given in Table 4.

Table 4

| Product | Alkylbenzene Sulfonic Acid (m) | Yield % |
|---|---|---|
| Dodecylbenzene-sulfonyl chloride | 5.82[1] | 94 |
| Pentadecylbenzene-sulfonyl chloride | 4.79[2] | 77[3] |

[1]The starting dodecylbenzenesulfonic acid was Bio Soft S-100$^R$, a biodegradable linear alkyl aryl sulfonic acid available from Stephan Chemical Co.
[2]The starting pentadecylbenzenesulfonic acid was Petrostep A-70 with an equivalent weight of 369 available from Stephan Chemical Co. The pentadecyl group was a branched chain hard alkylate group.
[3]Based on distillation of a 75 g. sample.

Dinonylnaphthalenesulfonyl chloride was prepared in the following manner. A mixture of 1 mole sodium dinonylnaphthalene sulfonate (NaSul 55 available from R. T. Vanderbilt Co. wherein the nonyl groups are branched chain) and phosphorous pentachloride (1.25 mole) was warmed very slowly on a steam bath with mechanical stirring. At approximately 40° C. there was very vigorous exotherming and some material was lost due to foaming. The reaction mixture was cooled and Skelly C (100 ml.) was added to lower the viscosity of the reaction mixture. The stirred reaction mixture was heated on a steam bath for 5 hours. The reaction mixture was then cooled, allowed to stand overnight and heated on a steam bath with the volatiles being stripped off under water aspirator vacuum. The residue was dissolved in Skelly C (1.5 liter). The Skelly C solution was washed with ice water, then brine, dried over sodium sulfate, filtered and evaporated to an oil (76% yield) in vacuo. The crude product analyzed as 6.6% Cl (theoretical = 7.2%) by X-ray and was used without purification in Example X to follow.

The preparation of sulfonyl chlorides from alkylhalides will be set forth in the Examples to follow in respect of the particular sulfonamidoquinolines being prepared therein. Likewise, where a substituted 8-aminoquinoline is used as the reactant in the preparation of the sulfonamidoquinolines, its preparation will be described in respect of each such particular sulfonamidoquinoline. 8-Aminoquinoline is commercially available and can also be prepared such as from 8-hydroxyquinoline or 8-nitroquinoline by any number of known procedures.

The following Examples illustrate preferred embodiments of the invention without being limiting. The first series of examples show the preparation of new sulfonamidoquinolines of the invention and the second series show metal extractions therewith.

EXAMPLE I-A

To a solution of 43.2 g. (0.3 mole) 8-aminoquinoline in 100 ml. pyridine and 200 ml. toluene was slowly added 103 g. (0.3 mole) dodecylbenzenesulfonyl chloride. The sulfonyl chloride was prepared as described above (see Table 2) from dodecylbenzene (Ucane Alkylate 12 obtained from Union Carbide which is a linear alkylate with average molecular weight of 244) and was an isomeric mixture wherein the dodecyl group is mostly in the para position. The reaction mixture was allowed to stir overnight. It was then heated to reflux for 1 hour and 500 ml. distilled water was added. Stirring was continued for an additional hour with heat after which the reaction mixture was poured into a separatory funnel. The phases were separated and one liter of Skelly C was added. Then the organic phase was washed two times with 25 g./l. aqueous $H_2SO_4$ (100 ml. portions), four times with freshly prepared 5% by weight $NaHCO_3$ in 40% aqueous methanol (200 ml. portions), two more times with the sulfuric acid solution (200 ml. portions), one more time with the sodium bicarbonate solution and then with brine. The reaction mixture was then dried over sodium sulfate, filtered and evaporated to dryness in vacuo. There was obtained 115.9 g. of product (85% yield, product was an oil) which was 8-(dodecylbenzenesulfonamido)quinoline having the structure

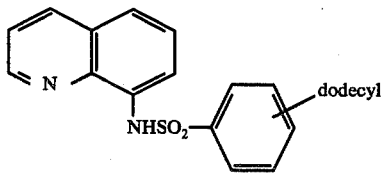

where the dodecyl group is as described in respect of the starting sulfonyl chloride. Structures were confirmed in this and succeeding Examples by Infra Red (IR) and Nuclear Magnetic Resonance (NMR) analyses.

EXAMPLE I-B

To a solution of 12.9 g. (0.09 mole) 8-aminoquinoline in 150 ml. pyridine was added 31.0 g. (0.09 mole) dodecylbenzenesulfonyl chloride in 100 ml. Skelly C at 0° C. The sulfonyl chloride was prepared from dodecylbenzenesulfonic acid (a technical grade of linear alkylate available from Pfaltz & Bauer) and the dodecyl group was mostly in the para position. The reaction mixture was stirred for 1 hour at 0° C. and then allowed to stir at room temperature overnight. It was then heated to 70° C. and poured into 600 ml. of ice water. The aqueous mixture was extracted with Skelly C and the resulting extract was washed four times with 5% by weight $NaHCO_3$ in 40% methanol-water. It was then dried over sodium sulfate, filtered, heated to boiling and 10 g. of decolorizing charcoal was added. The product solution was filtered through celite and evaporated to a pale yellow oil (32.3 g.) in vacuo. The product, 8-(dodecylbenzenesulfonamido)quinoline had the structure as defined in Example I-A above and where the dodecyl group was as in the starting dodecylbenzene.

EXAMPLE I-C

Example I-B was essentially repeated except that the starting dodecylbenzene was Chevron Alkylate 21 (available from Standard Oil of California which is a synthetic alkylbenzene in which the side chain is branched (hard alkylate) and contains an average of 12 carbon atoms) and the resulting sulfonyl chloride and 8-(dodecylbenzenesulfonamido)quinoline were isomeric mixtures wherein the dodecyl group was as in the starting dodecylbenzene (in this and succeeding Examples the alkyl groups on the ring are in the positions as in the starting alkylbenzenes or alkylbenzenesulfonyl chlorides and the sulfonamidoquinolines will thus normally be a mixture of isomers).

EXAMPLE II

To a 5 liter round bottom flask fitted with an air stirrer, thermometer, addition funnel and ice water bath were charged 365.7 g. (2.54 mole) 8-aminoquinoline and 2 liters pyridine. Then 838 g. (2.54 mole) decylmethylbenzenesulfonyl chloride was added slowly enough to maintain the temperature at 9°–13° C. (time of addition was 45 minutes). The sulfonyl chloride was that prepared in Run A of Table 2 from the decylmethylbenzene of Run B in Table 1. After addition of the sulfonyl chloride was completed, the reaction mixture was heated to room temperature and allowed to stir for 3 hours. It was then heated to 85° C. and held at 80° C. for 45 minutes after which 1 liter of water was added. The temperature was brought back to 80° C. and the water-reaction mixture held at that temperature for 30 minutes. The mixture was transferred to a 6 liter separatory funnel and 2 liters Skelly C and one liter water were added. After standing overnight, the phases were separated and 2 liters water were added to the aqueous phase which was then extracted with Skelly C and the Skelly C extract separated. The organic phases were combined and washed as follows: 3 times with 4% $NaHCO_3$ in 25% MeOH-water, 3 times with 25 g./l. aqueous $H_2SO_4$, 2 additional times with the $NaHCO_3$ solution, 2 additional times with the $H_2SO_4$ solution and then 1 time with brine. The product solution was dried over sodium sulfate and the Skelly C solvent was evaporated off giving 1066.9 g. of a light brown oil which was 8-(decylmethylbenzenesulfonamido)quinoline (90+% purity) having the structure

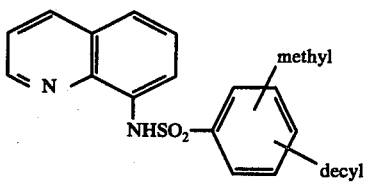

EXAMPLE III

Example II was essentially repeated except using 196 ml. pyridine, 36.0 g. (.25 mole) 8-aminoquinoline and 86.5 g. (0.25 mole) decylethylbenzenesulfonyl chloride. The said sulfonyl chloride was that prepared in Run A of Table 2 which in turn was prepared from the decylethylbenzene as prepared in Run A of Table 1. There was obtained 94 g. of a dark oil. The product was 8-(decylethylbenzenesulfonamido)quinoline having the structure

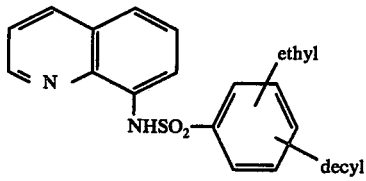

EXAMPLE IV

Example II was essentially repeated except using 120 ml. pyridine, 23.0 g. (.16 mole) 8-aminoquinoline and 56 g. (≅0.16 mole) dialkylbenzenesulfonyl chloride. The said sulfonyl chloride was that designated as $C_{11}$–$C_{14}$ alkylmethylbenzenesulfonyl chloride in Table 2 which in turn was prepared from the $C_{11}$–$C_{14}$ alkylmethylbenzene of Table 1. The product was a dark oil in a yield of 83%. It had the following structure

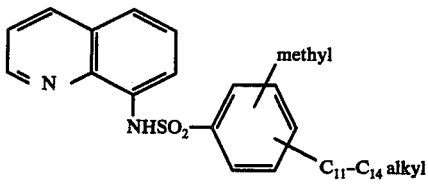

EXAMPLE V

Octyltoluene (50 g. - 0.245 mole) as prepared in Table 1 was added slowly at 5°–10° C. with stirring over ½ hour (some exotherm) to 81 g. (.69 mole) chlorosulfonic acid in a 250 ml. round bottom flask fitted with air stirrer, thermometer, addition funnel, reflux condenser, scrubber and ice bath. The reaction mixture was allowed to stir for 3 hours at 25°–30° C. and then stand overnight. It was poured onto 900 g. ice, 500 ml. diethyl ether was added and the mixture was stirred until the ice melted. The resulting organic phase was washed with water, 30% aqueous $Na_2CO_3$, again with water, dried over $Na_2SO_4$ and the solvent was evaporated. Thirty nine g. of octylmethylbenzenesulfonyl chloride was obtained.

To 14.4 g. (.10 mole) 8-aminoquinoline mixed with 14.4 g. (.15 mole) triethylamine and 25 ml. benzene was added 20.4 g. (0.067 mole) of the octylmethylbenzenesulfonyl chloride as above prepared at 14°–18° C. The reaction mixture was stirred for 2 hours at room temperature and then heated to 80° C. for 1 hour. Two hundred fifty ml. water and 250 ml. Skelly C were combined with the reaction mixture and the phases were allowed to separate overnight. The organic phase was washed as in Example II above, dried over $Na_2SO_4$ and stripped of solvent giving 26.7 g. of a dark oil which was 8-(octylmethylbenzenesulfonamido)quinoline having the structure:

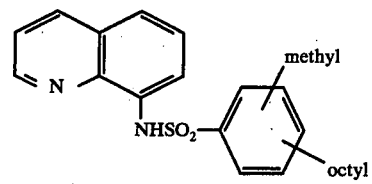

EXAMPLE VI

Example II was essentially repeated using 23.04 g. (0.16 mole) 8-aminoquinoline, 100 ml. pyridine and 49.5 g. (0.16 mole) of nonylmethylbenzenesulfonyl chloride as prepared in Table 2. The said nonylmethylbenzenesulfonyl chloride was in turn derived from a nonyltoluene having a branched nonyl group derived from tripropylene (available from Sunoco). There was obtained 55.1 g. of a dark oil which was 8-(nonylmethylbenzenesulfonamido)quinoline having the structure:

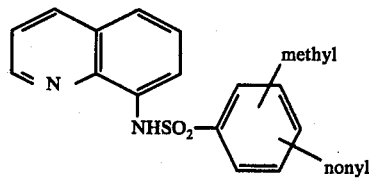

EXAMPLE VII

Example II was essentially repeated using 20 g. (0.139 mole) 8-aminoquinoline, 120 ml. pyridine and 50 g. (0.139 mole) decylisopropylbenzenesulfonyl chloride (also termed decylcumenesulfonyl chloride) as prepared in Table 2. The sulfonyl chloride was in turn derived from decylcumene as prepared in Table 1. There was obtained 50 g. of a dark viscous oil which was 8-(decylisopropylbenzenesulfonamido)quinoline having the structure:

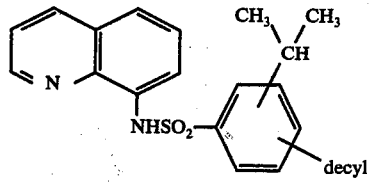

EXAMPLE VIII

Diamylbenzenesulfonyl chloride was prepared as in Table 3 above from diamylbenzene. The latter starting material was prepared in the following manner. To a suspension of 175.2 g. (1.29 mole) $AlCl_3$ in 660 ml. carbon tetrachloride was added 155.8 g. (1.29 mole) valeric acid chloride slowly so as not to bring the temperature of the ice-salt-water bath cooled reaction mixture above 5° C. (addition time was 20 min.). After this addition was complete, the mixture was cooled to 0° C. and addition of 159.2 g. (1.07 mole) of sec-amylbenzene (available from Phillips Petroleum) was begun (the addition was carried out at 0°-2° C. over a period of 3.5 hours). The reaction mixture was allowed to warm to 10° C. over a 1 hour period and was then dumped into an HCl-ice mixture and stirred overnight. The phases were allowed to separate, the aqueous was extracted with carbon tetrachloride and then the aqueous was discarded. The resulting organic phases were combined and washed as follows: 2 times with 7% wt./vol. aqueous HCl, 2 times with 10% by weight aqueous Na$_2$CO$_3$, 1 time with water and 2 times with brine. The product was dried over Na$_2$SO$_4$, stripped of solvent and distilled to yield fractions which were mostly p-sec-amyl-valerophenone (some ortho isomer was present). This product (104.8 g.) was mixed with 86.3 g. KOH, 61 ml. of 98 –100% NH$_2$NH$_2$.H$_2$O and 500 ml. diethylene glycol and heated to reflux. It was refluxed overnight and then heated from 140° C. (pot temp.) to 155° C. by collecting H$_2$O off the reaction mixture with a take-off condenser. The reaction mixture was heated at 195° C. for 1 hour with some refluxing, a total of 50 ml. of distillate was collected and it was then cooled and poured into 500 ml. water and 250 ml. of Skellysolve B (available from the Skelly Oil Co. and consists mostly of n-hexane, b.p. range 60°-71° C.). The phases were separated, the organic was washed 2 times with 10% aqueous HCl, dried over Na$_2$SO$_4$, filtered and evaporated to an oil. There was obtained 83.1 g. of product which was vacuum distilled to yield a 49.8 g. fraction (pot temp.—125°-145° C.; head temp.—105°-110° C.) which was diamylbenzene having the structure:

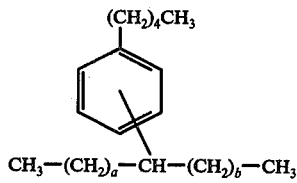

where $a + b$ equals 2.

The diamylbenzenesulfonyl chloride (25.5 g.-0.081 mole), as above prepared, 8-aminoquinoline (12.24 g.-0.085 mole), and 75 ml. pyridine were reacted in essentially the same manner as set forth in Example II to obtain 33.5 g. of 8-(diamylbenzenesulfonamido)quinoline having the structure:

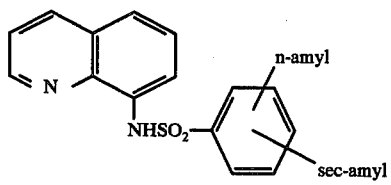

EXAMPLE IX

Example II was essentially repeated using 28.8 g. (0.2 mole) 8-aminoquinoline, 150 ml. pyridine and 49.35 g. (0.2 mole) 4-sec-amylbenzenesulfonyl chloride. There was obtained 50 g. of a thick oil which was 8-(sec-amylbenzenesulfonamido)quinoline having the structure

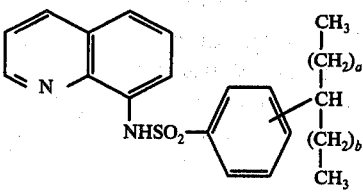

where $a + b$ equals 2.

EXAMPLE X

Dinonylnaphthalenesulfonyl chloride (125 g.-0.26 mole) prepared as described hereinabove was dissolved in 150 ml. toluene and added with stirring to a solution of 37 g. (0.26 mole) 8-aminoquinoline in 100 ml. pyridine while the temperature was maintained between 10°-20° C. (there was some exotherm). The reaction mixture was allowed to stir overnight at room temperature. It was then heated to 80° C. for 30 minutes after which 25 ml. conc. NH$_3$ was added and stirring was continued at 80° C. for 20 minutes. The reaction mixture was poured into 500 ml. Skelly C and 300 ml. water, the phases were separated and the organic was washed with 5% by weight NaHCO$_3$ (40% MeOH in water) until a good phase break was obtained. It was washed also with 25 g./l. H$_2$SO$_4$ until a good phase break was obtained. After these washings, the reaction mixture was heated to boiling, treated with five g. of decolorizing charcoal, dried over Na$_2$SO$_4$, filtered and evaporated to dryness in vacuo to give 152.2 g. of a black oil. The product was 8-(dinonylnaphthalenesulfonamide)quinoline of the structure

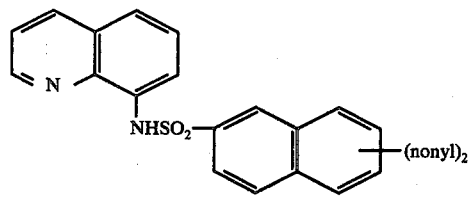

wherein the nonyl groups are as in the starting dinonylnaphthalene.

EXAMPLE XI

Example II was essentially repeated using 46.4 g. (0.32 mole) 8-aminoquinoline, 180 ml. pyridine and 82.35 g. (0.3 mole) heptylbenzenesulfonyl chloride. The latter reactant was as prepared in Table 2 from the heptylbenzene of Table 1. There was obtained 112.6 g. (97.35% yield) of 8-(heptylbenzenesulfonamido)quinoline of the structure

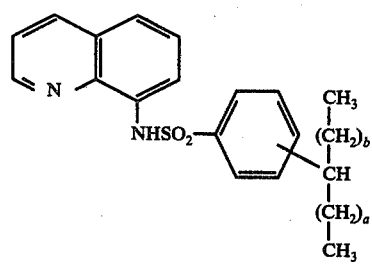

where $a + b$ equals 4.

EXAMPLE XII

Example II was essentially repeated using 28.8 g. (0.2 mole) 8-aminoquinoline, 50 ml. pyridine and 74.9 g. (0.2 mole) pentadecylbenzenesulfonyl chloride (see Table 4 for the preparation of the sulfonyl chloride). There was obtained 79.1 g. of 8-(pentadecylbenzenesulfonamido)-quinoline having the structure

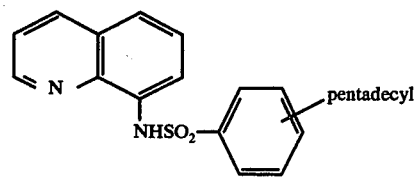

EXAMPLE XIII

Example II was essentially repeated using 36 g. (0.25 mole) 8-aminoquinoline, 100 ml. pyridine and 100 g. (0.25 mole) p-n-hexadecylbenzenesulfonyl chloride (see Table 3 above). There was obtained 24.6 g. (approximately two-thirds of reaction mixture was lost when a stop cock came out of a separatory funnel) of a yellow oil which crystallized. The product was 8-(p-n-hexadecylbenzenesulfonamido)quinoline having the structure:

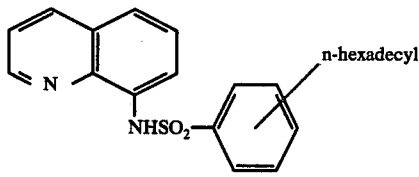

EXAMPLE XIV

Example XIII was essentially repeated using 22.68 g. (0.157 mole) 8-aminoquinoline, 75 ml. pyridine and 63 g. (0.157 mole) hexadecylbenzenesulfonyl chloride prepared as in Table 3 from the hexadecylbenzene of Table 1. There was obtained 49.25 g. (62% yield) of a golden oil which was 8-(hexadecylbenzenesulfonamido)quinoline of the structure

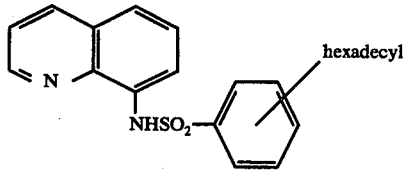

EXAMPLE XV

Example II was essentially repeated using 28.8 g. (0.2 mole) 8-aminoquinoline, 75 ml. pyridine and 60.4 g. (0.2 mole) 2,4,6-triisopropylbenzenesulfonyl chloride. There was obtained 71.4 g. of a purplish white solid which was 8-(2,4,6-triisopropylbenzenesulfonamido)-quinoline of the structure

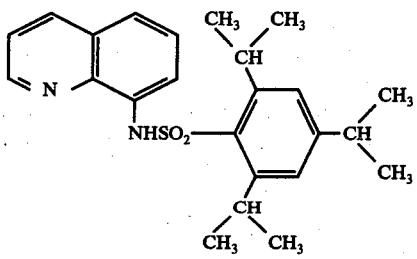

EXAMPLE XVI

Part A—Preparation of 2-methyl-8-aminoquinoline

To a cooled solution of 560 g. sodium metabisulfite in 1 liter of water was added 290 ml. ammonium hydroxide. This mixture was placed in a 2 liter stainless steel pressure reactor and 200 g. 8-hydroxyquinaldine was then added and the mixture was allowed to stand overnight. The reactor was sealed and heated to 150° C. The reaction mixture was then stirred at 150° C. for 7 hours during which period the pressure rose to 50 p.s.i.g. The reaction mixture was allowed to cool overnight with stirring and then the reactor was heated to 80° C. After reaching this temperature, the reactor was drained and washed with 1 liter of benzene at 70°–80° C. The benzene solution was added to the reaction mixture. The mixture was filtered and the phases separated. The organic was washed with dilute aqueous NaOH, then brine, dried over $Na_2SO_4$ and stripped of solvent to yield 84 g. of crude product. This was vacuum distilled to yield 50 g. of a yellow solid which was 2-methyl-8-aminoquinoline (also termed 8-aminoquinaldine).

Part B—Preparation of 8-(dodecylbenzenesulfonamido)-2-methylquinoline

Example II was essentially repeated using 79.8 g. (0.505 mole) of 2-methyl-8-aminoquinoline as prepared in Part A of this Example, 100 ml. pyridine in combination with 200 ml. toluene and 173.7 g. (0.505 mole) dodecylbenzenesulfonyl chloride as prepared in Table 4 above. The product was 8-(dodecylbenzenesulfonamido)-2-methylquinoline having the structure

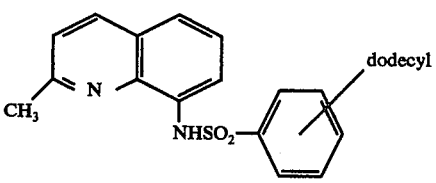

EXAMPLE XVII

Example XVI, Part B was essentially repeated using 25 g. (.158 mole) 2-methyl-8-aminoquinoline, 125 ml. pyridine and 52.3 g. (.158 mole) decylmethylbenzenesulfonyl chloride as prepared in Run B of Table 2. There was obtained 63.7 g. of 8-(decylmethylbenzenesulfonamido)-2-methylquinoline having the structure

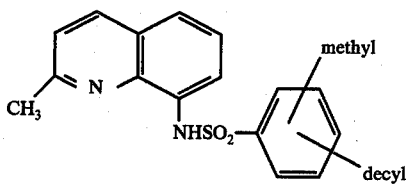

EXAMPLE XVIII

Part A—Preparation of 8-Amino-6-methylquinoline

Thirty g. 8-nitro-6-methylquinoline (prepared by the procedure of F. Richter and G. F. Smith, JACS, 66, 396 (1944)) was dissolved in 30 ml. ethylacetate, 50 ml. absolute ethanol and 50 ml. ethyl ether. This was divided into two parts and 0.4 g. $PtO_2$ added to each portion. Both were hydrogenated in a Parr shaker. Lots 1 and 2 were combined and distilled at pot temperatures of 110°–190° C. (0.45 mm Hg.). There was obtained 20.7 g. of high purity 8-amino-6-methylquinoline.

Part B—Preparation of 8-(decylmethylbenzenesulfonamido)-6-methylquinoline

Example II was essentially repeated using 19.4 g. (0.123 mole) of 8-amino-6-methylquinoline as prepared in Part A of this Example, 100 ml. pyridine and 41.3 g. (0.125 mole) decylmethylbenzenesulfonyl chloride as prepared in Run A of Table 2 above. There was obtained 51.4 g. of a light colored oil which was 8-(decylmethylbenzenesulfonamido)-6-methylquinoline of the structure

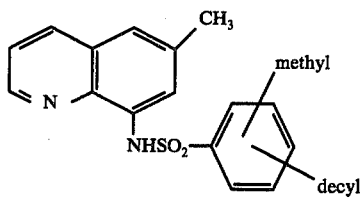

EXAMPLE XIX

Example XVIII, Part B was essentially repeated using 25 g. (0.14 mole) 8-amino-6-methoxyquinoline (available from Aldrich Chemical), 100 ml. pyridine and 47.3 g. (0.14 mole) of the decylmethylbenzenesulfonyl chloride. There was obtained 58.6 g. of a dark oil which was 8-(decylmethylbenzenesulfonamido)-6-methoxyquinoline having the structure

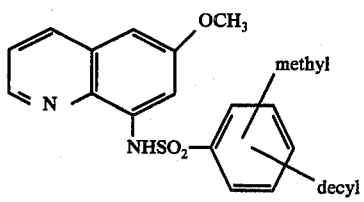

EXAMPLE XX

Part A—Preparation of 8-amino-5-nitroquinoline

To a five liter round bottom flask fitted with an air stirrer, condenser, addition funnel, thermometer and hot water bath were charged 40 g. (.23 mole) 5-nitroquinoline and 100 g. (1.44 mole) hydroxylamine hydrochloride. Then 1950 ml. of 95% EtOH was added and the solids dissolved after which 200 g. KOH in 1200 ml. MeOH was added over a 50 minute period at 54°–57° C. The mixture was allowed to stir at 55° C. for an additional hour and then dumped into 10 liters of water, allowed to cool and filtered. An orange solid was crystallized out of 95% ethanol. Such product was 8-amino-5-nitroquinoline.

Part B—Preparation of 8-(decylmethylbenzenesulfonamido)-5-nitroquinoline

Example II was essentially repeated using 18.9 g. (0.1 mole) 8-amino-5-nitroquinoline, 60 ml. pyridine and 36 g. (0.1 mole) decylmethylbenzenesulfonyl chloride as prepared in Run A of Table 2 above. Additionally, the reaction was heated at 80°–85° C. for 22–24 hours in contrast to the shorter heating period in Example II. There was obtained 13 g. of a dark oil which was 8-(decylmethylbenzenesulfonamido)-5-nitroquinoline of the formula

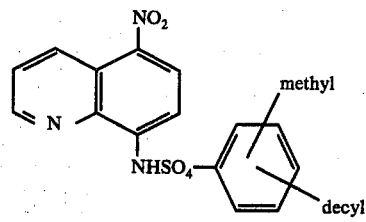

EXAMPLE XXI

Part A—Preparation of 8-Amino-5,7-dichloroquinoline

Chlorine gas was bubbled through a solution of 10 g. 8-aminoquinoline in 50 ml. of glacial acetic acid while the temperature was maintained at 40°–50° C. by cooling. The $Cl_2$ flow was stopped when the exotherming ceased (a total of 16.5 g. $Cl_2$ was added). The red precipitate was filtered from the reaction mixture and slurried with 100 ml. of 2% by weight aqueous NaOH and 300 ml. of ethyl ether. This mixture was filtered and the phases separated. The ether phase was washed with brine, dried over $Na_2SO_4$, filtered and evaporated to dryness to yield 5.6 g. crude product which was then recrystallized out of an ether-Skelly C mixture. There was obtained 5.1 g. of tan to brownish needles (melting point 121°–123° C.) which was 8-amino-5,7-dichloroquinoline.

Part B—Preparation of 8-(decylmethylbenzenesulfonamido)-5,7-dichloroquinoline Example XX, Part B was essentially repeated using 7.2 g. (0.034 mole) 8-amino-5,7-dichloroquinoline as prepared in Part A of this Example, 25 ml. pyridine and 11.9 g. (0.036 mole) decylmethylbenzenesulfonyl chloride as prepared in Run B of Table 2 above. There was obtained 12.2 g. of a reddish oil which was 8-(decylmethylbenzenesulfonamido)-5,7-dichloroquinoline having the structure

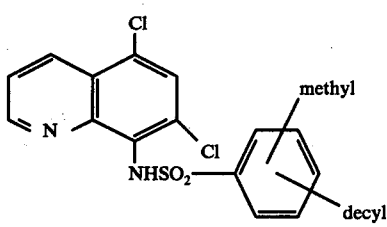

EXAMPLE XXII

Part A—Preparation of p-Dodecylphenylmethanesulfonyl chloride

A mixture of 147 g. (0.5 mole) dodecylbenzyl chloride (available as Conoco DBCl from Continental Oil Co. with the dodecyl group being a branched chain hard alkylate group), 79 g. (0.5 mole) anhydrous sodium thiosulfate, 250 ml. methanol, and 250 ml. distilled water was heated to reflux for 3 hours while stirring. Volatiles (about 75 ml.) were distilled off under aspirator vacuum until excessive foaming was encountered. The reaction mixture was transferred to a 2 liter flask fitted with a dry ice condenser, thermometer, mechanical stirrer and gas dispersion tube. The flask was cooled to 0° C. with an ice bath and then 250 ml. glacial acetic acid and 500 g. ice were added. Chlorine gas was bubbled in at a minimum rate to maintain a minimum amount of $Cl_2$ refluxing in the flask. The temperature was maintained at 10° C. or less ($Cl_2$ bubbled in for 1 hour). Five hundred ml. Skelly C were then added, the reaction mixture was stirred and the phases were separated. The organic phase was washed with 500 ml. of 50% by weight aqueous $NaHSO_3$, then with brine, dried over $Na_2SO_4$ and evaporated to give a golden oil. This product was partially purified by molecular distillation to yield p-dodecylphenylmethanesulfonyl chloride (approximate purity of 50%).

Part B—Preparation of 8-(dodecylphenylmethanesulfonamido)quinoline

The crude sulfonyl chloride as prepared in Part A of this Example was added directly to a stirring solution of 8-aminoquinoline (0.064 m) and triethylamine (0.07 m) in 25 ml. of 1,1,2-trichloroethane at 5°-10° C. The temperature was maintained at 5°-10° C. during the addition and then allowed to warm to room temperature. After stirring for 2 hours at room temperature, the reaction mixture was heated to 60° C. The reaction mixture was poured into 200 ml. of water and 300 ml. of Skelly C. After shaking, the phases were separated. The organic phase was washed three times with 100 ml. of 5% by weight of $NaHCO_3$ in 30% MeOH—$H_2O$, three times with 100 ml. of 25 g./l. sulfuric acid, repeat of bicarbonate washes, and finally with brine. The organic phase was dried over sodium sulfate and evaporated to dryness in vacuo. The reddish oil (50.4 gm; ≃30–50% sulfonamide by IR) was further purified by molecular distillation followed by column chromatography on silica gel to yield a viscous oil (8.2 gm., ≃75% sulfonamide). The compound had the structure

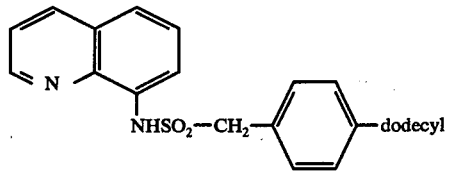

EXAMPLE XXIII

Example II was essentially repeated using 22.1 g. (0.154 mole) 8-aminoquinoline, 75 ml. pyridine and 50 g. (0.154 mole) n-hexadecanesulfonyl chloride. There was obtained 60.7 g. of 8-(n-hexadecanesulfonamido)quinoline having the formula

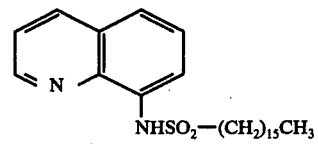

EXAMPLE XXIV

Part A—Preparation of 2-Ethylhexane-1-sulfonyl chloride

A mixture of 57.9 g. (0.3 mole) 2-ethylhexyl-1-bromide, 22.8 g. (0.3 mole) thiourea and 75 ml. absolute ethanol was allowed to stir at reflux for approximately 20 hours. After cooling overnight, the ethanol was evaporated in vacuo to yield a waxy white solid. This was dissolved in 250 ml. 80° C. water and 40% aqueous NaOH was added until no further white cloudiness formed in the aqueous. The oily product was separated and dissolved in 75 ml. acetic acid and 25 ml. water. This was cooled to 0° C. and $Cl_2$ was bubbled in until the oxidation reaction was complete (total $Cl_2$ use was 80.2 g.). The resulting colorless oil was 2-ethylhexane-1-sulfonyl chloride.

Part B—Preparation of 8-(2-ethylhexanesulfonamido)quinoline

Example II was essentially repeated using 43.2 g. (0.3 mole) 8-aminoquinoline, 200 ml. pyridine and the total amount of sulfonyl chloride as prepared in Part A of this Example. There was obtained 40.2 g. of product which was 8-(2-ethylhexanesulfonamido)quinoline having the structure

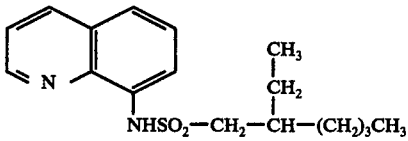

EXAMPLE XXV

Part A—Preparation of Isodecyl Bromide

One hundred ninety six g. (0.72 mole) $PBr_3$ was added slowly with stirring to 316 g. (2.0 mole) isodecanol (available from Union Carbide and is a mixture of isomeric alcohols containing ten carbon atoms) while maintaining the temperature below 0° C. After addition of the $PBr_3$ was complete, the reaction mixture was allowed to warm to room temperature while stirring was continued. The reaction mixture was allowed to stand overnight after attaching a drying tube to the reaction equipment. The crude product was distilled off at 60°–65° C. (0.45 mm Hg.), washed two times with cold $H_2SO_4$ (density = 1.84), two times with 50% MeOH—$NH_3$ and one time with brine, and dried over $CaCl_2$. The product was then further distilled to yield a 244.1 g. fraction (pot temp.—70° C., pressure—0.45 mm Hg. and head temp.—48° C.) of isodecylbromide.

Part B—Preparation of Isodecanesulfonyl chloride

A mixture of 110 g. (0.5 mole) of isodecylbromide as prepared in Part A of this Example, 38 g. (0.5 mole) thiourea and 250 ml. 95% ethanol was heated to reflux. Refluxing was continued for 8 hours and then the reaction mixture was cooled and allowed to stir over the weekend. Approximately 125 ml. ethanol was stripped off and a solution of 30 g. NaOH in 200 ml. water was added. The reaction mixture was again heated to reflux with stirring (three hours) after which it was poured into 300 ml. water and extracted with 200 ml. diethyl ether. The ether extract was dried over $Na_2SO_4$, filtered and evaporated to a slightly pink oil. This oil was dissolved in 250 ml. glacial acetic acid, 50 ml. of water was added, the mixture was cooled to 0° C. and sparging with $Cl_2$ gas was begun. Chlorine addition was very slow to avoid excessive heat evolution (temperature was controlled at approximately 0° C.). Chlorine was added until a refluxing atmosphere of $Cl_2$ was maintained for 1 hour (total $Cl_2$ addition was 137 g.). Excess $Cl_2$ was removed by a $N_2$ sparge into $NaHSO_3$ solution. The reaction mixture was poured into 500 ml. water and then extracted with hexane. The hexane extract was washed two times with 5% by weight aqueous $NaHSO_3$ and one time with brine, dried over $Na_2SO_4$, filtered and evaporated in vacuo to a white oil. There was obtained 107 g. of isodecanesulfonyl chloride.

Part C—Preparation of 8-(Isodecanesulfonamido)quinoline

Example II was essentially repeated using 43.2 g. (0.3 mole) 8-aminoquinoline, 200 ml. pyridine and 72 g. (0.3 mole) of isodecanesulfonyl chloride as prepared in Part B of this Example. There was obtained 92.0 g. of 8-(isodecanesulfonamido)quinoline having the structure

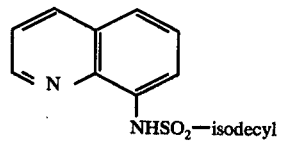

where the isodecyl group was characterized by NMR as follows: $CH_2CH_2(C_8H_{17})$ where the $C_8H_{17}$ group is a mixture of branched chain alkyl groups.

EXAMPLE XXVI

Part A—Preparation of $C_{14}$–$C_{16}$ alkenylsulfonyl chloride

A mixture of 84.3 g. (0.405 mole) $PCl_5$ and 96.7 g. (0.324 mole) of a sodium $C_{14}$–$C_{16}$ alkenyl sulfonate (Bio Terge$^R$ AS-90F available from Stephan Chemical Co.) was placed in a 500 ml. three-neck round bottom flask fitted with a condenser and mechanical stirrer. The mixture was heated on a steam cone for 2 hours with stirring. The initial reaction was very vigorous and exothermic. Addition of 50 ml. Skelly C was followed by distillation under water aspirator vacuum on the steam cone. The residue was dissolved in 300 ml. Skelly C and the resulting solution was filtered. The solution was evaporated in vacuo to an oil (62.5 g.) which was used in Part B of this Example.

Part B—Preparation of 8-($C_{14}$-$C_{16}$-alkenylsulfonamido)quinoline

The sulfonyl chloride prepared in Part A was added slowly to a stirring solution of 30.6 g. (0.212 mole) 8-aminoquinoline in 100 ml. pyridine at a temperature of 10°–20° C. The reaction mixture was allowed to stir overnight at room temperature. It was then heated to 80° C., 200 ml. of water was added, and after 30 minutes 25 ml. of 28% aqueous ammonia was added. The mixture was poured into 300 ml. of water and 500 ml. of Skelly C. The phases were separated and the organic phase was washed with methanolic sodium bicarbonate and then with 25 g./l. sulfuric acid. The acid wash generated an emulsion, which was allowed to break over the weekend. The organic was washed with methanolic sodium bicarbonate until a good phase break was obtained. The organic was then dried over anhydrous sodium sulfate, filtered, treated with 5 g. of norite, filtered and evaporated to an oil. The oil was passed through a 100 g. silica gel column with 1 l. of Skelly C. The Skelly C was evaporated in vacuo to 41.8 g. of an oil. The oil was further purified by molecular distillation. Some decomposition was evident during the distillation. The distillation yielded 10.1 g. of an oil that was estimated to be 60–65% sulfonamide by IR and NMR. The sulfonamidoquinoline active portion of the product had the formula

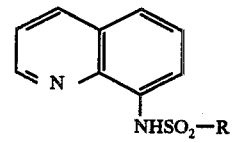

where R is the $C_{14}$–$C_{16}$ alkenyl group.

EXAMPLE XXVII

Example II was essentially repeated using 21.6 g. (0.15 mole) 8-aminoquinoline, 100 ml. pyridine and 31.8 g. (0.15 mole) n-octanesulfonyl chloride. There was obtained 39.2 g. of a yellow oil which was 8-(n-octanesulfonamido)quinoline having the structure

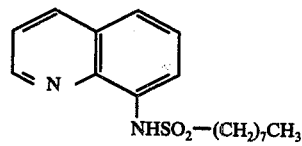

EXAMPLE XXVIII

Example II was essentially repeated using 45 g. (0.26 mole) crude n-pentanesulfonyl chloride, 37.4 g. (0.26 mole) 8-aminoquinoline and 150 ml. pyridine. There was obtained 35.6 g. of product which was 8-(n-pentanesulfonamido)quinoline having the structure

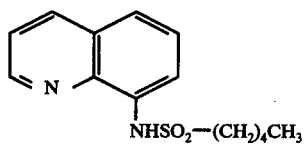

NHSO$_2$—(CH$_2$)$_4$CH$_3$

The Examples to follow show the use of the new sulfonamidoquinolines in the extraction of metals from their aqueous solutions. Unless otherwise indicated, the extractions were carried out in accordance with the following process procedures.

PROCEDURE 1

A 0.1 molar solution of the sulfonamidoquinoline in an identified essentially water-immiscible solvent is first prepared. Five aqueous solutions of the following compositions are used:

| Metal | Composition |
|---|---|
| $Cu^{++}$ | 0.05 M CuSO$_4$ (3.2 g./l. $Cu^{++}$), 0.4 M NH$_3$, and 0.1 M (NH$_4$)$_2$SO$_4$ |
| $Ni^{++}$ | 0.05 M NiSO$_4$ (2.9 g./l. $Ni^{++}$), 0.4 M NH$_3$, and 0.1 M (NH$_4$)$_2$SO$_4$ |
| $Zn^{++}$ | 0.05 M ZnSO$_4$ (3.2 g./l. $Zn^{++}$), 0.4 M NH$_3$, and 0.1 M (NH$_4$)$_2$SO$_4$ |
| $Co^{++}$ | 0.025 M CoSO$_4$ (1.5 g./l. $Co^{++}$), 1.7 M NH$_3$, and 0.1 M (NH$_4$)$_2$SO$_4$ prepared as needed under an atmosphere of nitrogen |
| $Co^{+++}$ | 0.025 M CoSO$_4$ (1.5 g./l. $Co^{++}$), 1.7 M NH$_3$, and 0.1 M (NH$_4$)$_2$CO$_3$ (air oxidized to $Co^{+++}$) |

Portions of the organic solution are shaken with the various aqueous solutions at an organic:aqueous phase ratio of 1:1 for one hour at ambient temperature. The organic phases are then analyzed for metal content. If a third phase is present, both the organic and aqueous phases are clarified and analyzed.

PROCEDURE 2

In this procedure, the purpose is to determine the extent of extraction of various metal ions as a function of pH over the pH range 1-6. A 0.1 molar solution of the sulfonamidoquinoline in an identified essentially water-immiscible organic solvent is prepared as in Procedure 1. Portions thereof are then contacted at an organic:aqueous phase ratio of 1:1 with shaking for one hour at ambient temperature. The aqueous phases are made up from equivolumes of two components:

Component A—0.2 M metal sulfate solution in water
Component B—water or sulfuric acid or sodium hydroxide solutions ranging from 0.005 M to 0.5 M Several extractions are performed at varying pH values. The first is done using water as component B. After determining raffinate pH, Component B is then selected such that raffinate pH values range from about 1 to 6 in units of approximately 1. By analyzing the organic phases for metal extraction and the aqueous for pH, data is generated which gives the degree of metal extraction as a function of pH for the particular system under study.

PROCEDURE 3

The objective of this process procedure is to determine the extent of extraction of the various metal ions as a function of total ammonia concentration in the aqueous phase. Organic solutions of the sulfonamidoquinoline are prepared as in the previous procedures and contacted with shaking at 1:1 organic:aqueous phase ratios for one hour at ambient temperatures with aqueous solutions made up as follows:

| Aqueous Solution | Metal Sulfate conc. | NH$_3$ conc. | (NH$_4$)$_2$SO$_4$ conc. | Total NH$_3$ conc. |
|---|---|---|---|---|
| 1 | 0.005M | 0.60M | 0.15M | 0.90M (15.3 g./l.) |
| 2 | 0.005M | 1.20M | 0.30M | 1.80M (30.6 g./l.) |
| 3 | 0.005M | 2.40M | 0.60M | 3.60M (61.2 g./l.) |
| 4 | 0.005M | 3.60M | 0.90M | 5.40M (91.8 g./l.) |
| 5 | 0.005M | 4.80M | 1.20M | 7.20M (122.4 g./l.) |
| 6 | 0.005M | 6.00M | 1.50M | 9.00M (153.0 g./l.) |

The separated organic and aqueous phases are analyzed for metal concentration. The effect of increasing ammonia concentration on degree of extraction can thus be determined.

PROCEDURE 4

The objective of this procedure is three-fold: (1) To determine the extent of metal stripping as a function of acid concentration; (2) To determine the extent of ammonia loading during extraction; and (3) To determine the extent of acid loading during stripping. Organic solvent solutions are prepared as in the other procedures and the following aqueous solutions are prepared:

A. 0.1M metal sulfate, 0.6M NH$_3$ and 0.15M (NH$_4$)$_2$SO$_4$
B. Five solutions containing 25, 50, 75, 100 and 150 g./l. H$_2$SO$_4$, respectively.

In the first step, the sulfonamidoquinoline solution is contacted with aqueous solution A at an organic:aqueous phase ratio of 1:2 with shaking for 1 hour at ambient temperatures. The phases are separated and the loaded organic contacted a second time as indicated with fresh aqueous Solution A. The resulting separated organic phase is analyzed for metal concentration. It is divided into five portions, each of which is shaken with one of the five aqueous B solutions (organic:aqueous phase ratio of 1:1, contact time—1 hour). The phases are separated and the organics are analyzed for metal content, the aqueous for NH$_3$. The stripped organics are then washed with water at an organic:aqueous phase ratio of 1:1 (contact time—1 hour). The aqueous wash solutions are then analyzed for H$_2$SO$_4$.

EXAMPLE A

A 0.1M solution of the 8-(dodecylbenzenesulfonamido)quinoline of Example I B in an aromatic kerosene (Aromatic 150) was first prepared. This was then used in accordance with Procedure 1 and the following results were obtained:

| Metal | Organic g./l. metal |
|---|---|
| $Co^{+3}$ | 0.0170 |
| $Cu^{++}$ | 3.06 |
| $Ni^{++}$ | 2.75 |
| $Zn^{++}$ | 3.87 |

This same process when run with a solution of the sulfonamidoquinoline in an aliphatic kerosene (Kermac 470 B) gave good extraction of $Co^{++}$ (1.35 g./l.) but precipitates formed with $Cu^{++}$ and $Ni^{++}$ and the organic phase gelled with $Zn^{++}$. Thus for this sulfonamidoquinoline, a more aromatic solvent yields best results.

The Aromatic 150 solution of the 8-(dodecylbenzenesulfonamido)quinoline was used in accordance with process Procedure 2 to study the pH isotherms for $Cu^{++}$, $Zn^{++}$, $Co^{++}$, $Fe^{+++}$, and $Ni^{++}$. Results are set forth in the following Tables A-1 through A-5. In all cases, 10 ml. of the sulfonamidoquinoline solution and 5 ml. of the 0.2M metal sulfate solutions were used with varying amounts (in milliliters) of water and NaOH and/or $H_2SO_4$ solutions as indicated.

Table A-1

| | | | | | $Cu^{++}$ | |
|---|---|---|---|---|---|---|
| | NaOH | | $H_2SO_4$ | | Extracted Aqueous | $Cu^{++}$ Organic |
| $H_2O$ | 0.1M | 0.5M | 0.1M | 0.5M | pH | g./l. |
| 5.0 | 0 | 0 | 0 | 0 | 1.56 | 2.45 |
| 4.5 | 0.5 | 0 | 0 | 0 | 1.69 | 2.53 |
| 4.0 | 1.0 | 0 | 0 | 0 | 1.63 | 2.55 |
| 3.5 | 1.5 | 0 | 0 | 0 | 1.66 | 2.54 |
| 3.0 | 2.0 | 0 | 0 | 0 | 1.67 | 2.58 |
| 4.5 | 0 | 0 | 0.5 | 0 | 1.54 | 2.43 |
| 0 | 5.0 | 0 | 0 | 0 | 1.98 | 2.88 |
| 3.0 | 0 | 2.0 | 0 | 0 | 4.40* | 3.04 |
| 3.0 | 0 | 0 | 2.0 | 0 | 1.44 | 2.25 |
| 3.5 | 0 | 0 | 0 | 1.5 | 2.24 | 2.94 |
| 3.0 | 0 | 0 | 0 | 2.0 | 0.83 | 1.62 |
| 1.0 | 0 | 0 | 0 | 4.0 | 0.60 | 1.02 |

*Slight precipitate observed

Table A-2

| | | | | | $Zn^{++}$ | |
|---|---|---|---|---|---|---|
| | NaOH | | $H_2SO_4$ | | Extracted Aqueous | $Zn^{++}$ Organic |
| $H_2O$ | 0.1M | 0.5M | 0.1M | 0.5M | pH | g./l. |
| 5 | 0 | 0 | 0 | 0 | 3.03 | 0.116 |
| 0 | 5 | 0 | 0 | 0 | 4.10 | 2.04 |
| 0 | 0 | 0 | 5 | 0 | 1.21 | 0.00054 |
| 4 | 0 | 0 | 1 | 0 | 2.23 | 0.00203 |
| 2 | 0 | 0 | 3 | 0 | 1.73 | 0.0004 |
| 3 | 0 | 0 | 0 | 2 | 1.12 | 0.00074 |
| 4 | 1 | 0 | 0 | 0 | 3.59 | 0.461 |
| 2 | 3 | 0 | 0 | 0 | 3.96 | 1.20 |
| 3 | 0 | 2 | 0 | 0 | 6.18* | 3.40 |

*Some precipitate observed

Table A-3

| | | | | | $Co^{++}$ | |
|---|---|---|---|---|---|---|
| | NaOH | | $H_2SO_4$ | | Extracted Aqueous | $Co^{++}$ Organic |
| $H_2O$ | 0.1M | 0.5M | 0.1M | 0.5M | pH | g./l. |
| 5 | 0 | 0 | 0 | 0 | 3.48 | 0.0028 |
| 0 | 5 | 0 | 0 | 0 | 5.21 | 1.46 |
| 0 | 0 | 0 | 5 | 0 | 1.29 | 0.0002 |
| 3 | 0 | 2 | 0 | 0 | 7.25* | 2.72 |
| 2 | 3 | 0 | 0 | 0 | 5.41 | 0.860 |
| 4 | 1 | 0 | 0 | 0 | 4.94 | 0.275 |
| 3 | 0 | 0 | 0 | 2 | 1.17 | 0.0002 |
| 2 | 0 | 0 | 3 | 0 | 1.70 | 0.0008 |
| 4 | 0 | 0 | 1 | 0 | 2.18 | <0.0002 |

*Some precipitate observed

Table A-4

| | | | | | $Fe^{+++}$ | |
|---|---|---|---|---|---|---|
| | NaOH | | $H_2SO_4$ | | Extracted Aqueous | $Fe^{+++}$ Organic |
| $H_2O$ | 0.1M | 0.5M | 0.1M | 0.5M | pH | g./l. |
| 5 | 0 | 0 | 0 | 0 | 1.77 | 0.00017 |
| 0 | 5 | 0 | 0 | 0 | 2.26* | 0.00033 |
| 0 | 0 | 0 | 5 | 0 | 1.19 | 0.00011 |
| 3 | 0 | 2 | 0 | 0 | 2.44* | 0.00045 |
| 1 | 0 | 4 | 0 | 0 | 2.59* | 0.00063 |
| 3 | 0 | 0 | 0 | 2 | 0.90 | 0.00012 |

*Precipitate observed

Table A-5

| | | | $Ni^{++}$ | |
|---|---|---|---|---|
| | NaOH | $H_2SO_4$ | Extracted Aqueous | $Ni^{++}$ Organic |
| $H_2O$ | 0.1M | 0.1M | pH | g./l. |
| 5.0 | 0 | 0 | 3.51 | 0.0425 |
| 2.0 | 3.0 | 0 | 7.11 | 0.840 |
| 3.0 | 2.0 | 0 | 4.83 | 0.610 |
| 3.5 | 1.5 | 0 | 4.33 | 0.477 |
| 4.5 | 0.5 | 0 | 3.93 | 0.183 |
| 4.75 | 0.25 | 0 | 3.74 | 0.101 |
| 0 | 0 | 5.0 | 1.33 | 0.0002 |
| 3.0 | 0 | 2.0 | 1.67 | 0.0003 |
| 4.0 | 0 | 1.0 | — | 0.0004 |

The data of Tables A-1 through A-5 show extractions for $Cu^{++}$, $Co^{++}$, $Zn^{++}$ and $Ni^{++}$ and substantially no extraction of $Fe^{+++}$ indicating excellent selectivity of $Cu^{++}$, for example, over $Fe^{+++}$ at relatively low pH's.

The process of Procedure 3 was also used with the 8-(dodecylbenzenesulfonamido)quinoline solution (Aromatic 150). Results are set forth in the following Tables A-6 through A-8:

Table A-6

| $Cu^{++}$ | |
|---|---|
| Metal Concentration (g./l.) | |
| Loaded Organic | Aqueous Raffinate |
| 0.317 | 0.0002 |
| 0.314 | 0.0002 |
| 0.310 | 0.0002 |
| 0.316 | 0.0002 |
| 0.322 | 0.0006 |
| 0.302 | 0.0014 |

Table A-7

| $Ni^{++}$ | |
|---|---|
| Metal Concentration (g./l.) | |
| Loaded Organic | Aqueous Raffinate |
| 0.299 | 0.0003 |
| 0.299 | 0.0012 |
| 0.305 | 0.0032 |
| 0.278 | 0.0342 |
| 0.202 | 0.118 |
| 0.140 | 0.184 |

Table A-8

| $Zn^{++}$ | |
|---|---|
| Metal Concentration (g./l.) | |
| Loaded Organic | Aqueous Raffinate |
| 0.456 | <0.0005 |
| 0.445 | <0.0005 |
| 0.448 | 0.0029 |
| 0.424 | 0.0150 |
| 0.414 | 0.0346 |
| 0.379 | 0.0710 |

The process of Procedure 4 was also followed with the Aromatic 150 solution of the 8-(dodecylbenzenesulfonamido)quinoline in respect of $Cu^{++}$, $Ni^{++}$ and $Zn^{++}$. Results are set forth in the following Tables A-9 through A-11:

Table A-9

| | | $Cu^{++}$ | | |
|---|---|---|---|---|
| | Loaded Organic From Step 2 — 2.99 g./l. $Cu^{++}$ | | | |
| Strip Solution g./l. $H_2SO_4$ | Stripped Org. g./l. $Cu^{++}$ | Aqueous Raffinate $NH_3$—M | Washed Org. g./l. $Cu^{++}$ | Wash Solution $H_2SO_4$—N* |
| 25 | 1.15 | 0.002 | 1.15 | <0.001 |
| 50 | 0.563 | 0.003 | 0.560 | " |
| 75 | 0.267 | 0.003 | 0.253 | " |
| 100 | 0.144 | 0.010 | 0.143 | " |

Table A-9-continued

Cu$^{++}$
Loaded Organic From Step 2 — 2.99 g./l. Cu$^{++}$

| Strip Solution g./l. H$_2$SO$_4$ | Stripped Org. g./l. Cu$^{++}$ | Aqueous Raffinate NH$_3$—M | Washed Org. g./l. Cu$^{++}$ | Wash Solution H$_2$SO$_4$—N* |
|---|---|---|---|---|
| 150 | ≈0.05 | 0.003 | 0.0580 | " |

*Normality

Table A-10

Ni$^{++}$
Loaded Organic From Step 2 — 2.80 g./l. Ni$^{++}$

| Strip Solution g./l. H$_2$SO$_4$ | Stripped Org. g./l. Ni$^{++}$ | Aqueous Raffinate NH$_3$—M | Washed Org. g./l. Ni$^{++}$ | Wash Solution H$_2$SO$_4$—N |
|---|---|---|---|---|
| 25 | 0.294 | 0.068 | — | <0.001 |
| 50 | 0.050 | 0.069 | 0.075 | " |
| 75 | 0.0007 | 0.067 | 0.0012 | " |
| 100 | 0.0012 | 0.067 | 0.0016 | " |
| 150 | 0.0005 | 0.067 | 0.0006 | " |

Table A-11

Zn$^{++}$
Loaded Organic From Step 2 — 3.92 g./l. Zn$^{++}$

| Strip Solution g./l. H$_2$SO$_4$ | Stripped Org. g./l. Zn$^{++}$ | Aqueous Raffinate NH$_3$—M | Washed Org. g./l. Zn$^{++}$ | Wash Solution H$_2$SO$_4$—N |
|---|---|---|---|---|
| 25 | 0.0019 | 0.020 | 0.0007 | <0.001 |
| 50 | 0.0014 | 0.021 | 0.0008 | " |
| 75 | 0.0010 | 0.020 | 0.0006 | " |
| 100 | 0.0009 | 0.020 | 0.0005 | " |
| 150 | 0.0009 | 0.018 | 0.0008 | " |

The above data show that the metal values are readily stripped from the loaded organic and that the 8-(dodecylbenzenesulfonamido)quinoline loads very little sulfuric acid.

In processes as described above in this Example, the solubility of certain metal complexes, especially zinc, is best by using the 8-(dodecylbenzenesulfonamido)quinoline of Example I-A or I-B instead of I-C. In this respect, the branching in the dodecyl group is different as generally described hereinabove.

EXAMPLE B

A 0.1M solution of the 8-(decylmethylbenzenesulfonamido)quinoline of Example II in Kermac 470B aliphatic kerosene was first prepared. This was then used in accordance with process Procedure 1 and the following results were obtained:

Table B-1

| Metal | Organic, g./l. metal |
|---|---|
| Cu$^{++}$ | 3.04 |
| Ni$^{++}$ | —* |
| Co$^{++}$ | 1.46 |
| Co$^{+++}$ | <0.0005 |
| Zn$^{++}$ | 2.99 |

*The starting aqueous contained 2.69 g./l. Ni$^{++}$. There was some precipitate so the aqueous raffinate was analyzed rather than the organic. The raffinate contained only 0.0080 g./l. Ni$^{++}$. Subsequent tests with Ni$^{++}$ showed little or no precipitation.

The aliphatic kerosene (Kermac 470B) solution of the sulfonamidoquinoline of Example II was also used in accordance with process Procedure 2 to study the pH isotherms for Cu$^{++}$, Ni$^{++}$, Co$^{++}$, Zn$^{++}$ and Fe$^{+++}$. Results are set forth in the following Table B-2 (same quantities of phases and the like as in Example A above except herein the equivolume of aqueous phase mixed with the metal containing solution is indicated as being H$_2$O or specified molarities of NaOH or H$_2$SO$_4$):

Table B-2

| Metal | pH Adjusting Solution | Cu$^{++}$ Extracted Aqueous pH | Metal Organic g./l. |
|---|---|---|---|
| Cu$^{++}$ | 0.5M H$_2$SO$_4$ | 0.66 | 0.565 |
| " | 0.1M H$_2$SO$_4$ | 1.17 | 1.98 |
| " | 0.05M | 1.22 | 1.98 |
| " | H$_2$O | 1.38 | 2.30 |
| " | 0.005M NaOH | 1.41 | 2.34 |
| " | 0.05M NaOH | 1.68 | 2.46 |
| " | 0.1M NaOH | 1.77 | 2.65 |
| Ni$^{++}$ | 0.5M H$_2$SO$_4$ | 0.60 | <0.0005 |
| " | 0.1M H$_2$SO$_4$ | 1.59 | <0.0005 |
| " | 0.05M H$_2$SO$_4$ | 1.68 | <0.0005 |
| " | H$_2$O | 3.92 | 0.0057 |
| " | 0.005M NaOH | 4.77 | 0.0785 |
| " | 0.05M NaOH | 6.76* | 0.397 |
| Co$^{++}$ | 0.5M H$_2$SO$_4$ | 0.59 | <0.0005 |
| " | 0.1M H$_2$SO$_4$ | 1.59 | <0.0005 |
| " | 0.05M H$_2$SO$_4$ | 1.67 | <0.0005 |
| " | H$_2$O | 3.38 | <0.0005 |
| " | 0.005M NaOH | 4.73 | 0.0510 |
| " | 0.05M NaOH | 5.54 | 0.635 |
| " | 0.1M NaOH | 7.00* | 1.00 |
| Zn$^{++}$ | 0.5M H$_2$SO$_4$ | 0.6 | <0.0005 |
| " | 0.1M H$_2$SO$_4$ | 1.57 | <0.0005 |
| " | 0.05M H$_2$SO$_4$ | 1.67 | <0.0005 |
| " | H$_2$O | 3.36 | 0.0501 |
| " | 0.005M NaOH | 3.54 | 0.113 |
| " | 0.5M NaOH | 4.03 | 0.780 |
| " | 0.1M NaOH | 4.34 | 1.52 |
| Fe$^{+++}$ | (at pH's 0.59 – 2.00$^+$ — less than 0.0005 g./l. Fe$^{+++}$ extracted) | | |

*Precipitate in aqueous observed at this pH indicating that the metal oxide was precipitating.

Similarly when the 8-(decylmethylbenzenesulfonamido)quinoline is dissolved in Aromatic 150 and used according to the Procedure 2 process, cadmium is extracted as follows:

Table B-3

| pH Adjusting Solution | Cd$^{++}$ Extracted Aqueous pH | Cd$^{++}$ Organic g./l. |
|---|---|---|
| 0.5M H$_2$SO$_4$ | 0.82 | 0.00015 |
| 0.1M H$_2$SO$_4$ | 1.76 | 0.00028 |
| H$_2$O | 4.10 | 0.00240 |
| 0.05M NaOH | 5.52 | 1.21 |
| 0.1M NaOH | 5.89* | 1.53 |

*See footnote to Table B-2

The process of Procedure 3 was used with the aliphatic kerosene (Kermac 470B) solution of 8-(decylmethylbenzenesulfonamido)quinoline. Results are set forth in the following Table B-4:

Table B-4

| Metal | Metal Concentration In Organic g./l. |
|---|---|
| Cu$^{++}$ | 0.315 |
| " | 0.315 |
| " | 0.306 |
| " | 0.316 |
| " | 0.318 |
| " | 0.319 |
| Ni$^{++}$ | 0.296 |
| " | — |
| " | 0.300 |
| " | 0.309 |
| " | 0.283 |
| " | 0.230 |
| Zn$^{++}$ | 0.343 |
| " | 0.346 |
| " | 0.334 |
| " | 0.308 |
| " | 0.259 |
| " | 0.211 |

Procedure 4 processing was followed with the aliphatic kerosene-sulfonamido solution with results being set forth in the following Tables (stripped organic, NH₃ in raffinate and pH of water wash data only were collected):

Table B-5

Loaded Organic From Step 2 — 3.04 g./l. $Cu^{++}$

| Strip Solution g./l. $H_2SO_4$ | Stripped Organic g./l. $Cu^{++}$ | Aqueous Raffinate $NH_3$—M | Wash Solution pH |
|---|---|---|---|
| 25 | 0.895 | 0.0043 | 7.7 |
| 50 | 0.311 | 0.0052 | 7.4 |
| 75 | 0.124 | 0.0026 | 7.2 |
| 100 | 0.075 | 0.0030 | 7.1 |
| 150 | 0.008 | 0.0060 | 6.6 |

Table B-6

Loaded Organic* From Step 2 — about 2.5 g./l. $Ni^{++}$

| Strip Solution g./l. $H_2SO_4$ | Stripped Organic g./l. $Ni^{++}$ | Aqueous Raffinate $NH_3$—M | Wash Solution pH |
|---|---|---|---|
| 25 | <0.0005 | 0.036 | 7.4 |
| 50 | " | 0.0037 | 7.5 |
| 75 | " | 0.033 | 7.3 |
| 100 | " | 0.0037 | 7.1 |
| 150 | " | 0.030 | 8.1 |

*The starting loaded organic was not analyzed, thus the $Ni^{++}$ content was estimated.

Table B-7

$Zn^{++}$
Loaded Organic From Step 2 — 2.99 g./l. $Zn^{++}$

| Strip Solution g./l. $H_2SO_4$ | Stripped Organic g./l. $Zn^{++}$ | Aqueous Raffinate $NH_3$—M | Wash Solution pH |
|---|---|---|---|
| 25 | <0.0005 | 0.011 | 7.6 |
| 50 | " | 0.014 | 6.8 |
| 75 | " | 0.012 | 7.3 |
| 100 | " | 0.014 | 7.3 |
| 150 | " | 0.012 | 7.3 |

To further check the low sulfuric acid loading property of the sulfonamidoquinolines, the 0.1M solution of 8-(decylmethylbenzenesulfonamido)quinoline in Kermac 470B kerosene was contacted (1 hour, organic-:aqueous phase ratio of 2:1) with $H_2SO_4$ stripping solutions. This was followed by water washing and pH analysis of the wash solution. Results were as follows:

Table B-8

| Aqueous g./l. $H_2SO_4$ | Water Wash pH |
|---|---|
| 100 | 5.38 |
| 150 | 5.83 |
| 200 | 4.90 |
| 250 | 4.42 |

In a further process to determine the kinetics of loading and stripping of $Cu^{++}$, a 4% wt./vol. solution of the 8-(decylmethylbenzenesulfonamido)quinoline of Example II in Kermac 470B was contacted at a 1:1 organic-:aqueous phase ratio with an aqueous solution containing 4.0 g./l. $Cu^{++}$ (as $CuSO_4$) and 4.0 g./l. $Fe^{+++}$ (as $Fe_2(SO_4)_3$) adjusted to a pH of 1.9 and samples ere removed for analysis at designated times. Likewise, a $Cu^{++}$ loaded organic was contacted with an aqueous stripping solution which initially contained 28 g./l. $Cu^{++}$ (as $CuSO_4$) and 148 g./l. $H_2SO_4$ (organic:aqueous phase ratio of 1:1) and samples were also removed at designated time periods. The extraction and stripping were carried out in a mixer box having inside dimensions of 2¼ × 2¼ by 4 inches and mixing was provided by a 1¼ inch impellor spinning at 2000 rpm. Under these conditions both the extraction and stripping were at 95% equilibrium in 45 seconds. The results are set forth in Table B-9 which follows:

Table B-9

| Time | Loading Organic g./l. $Cu^{++}$ | Loading Organic g./l. $Fe^{+++}$ | Stripping Organic g./l. $Cu^{++}$ |
|---|---|---|---|
| 0 | 0.04 | <0.0005¹ | 2.47 |
| 15 sec. | 1.49 | " | 0.76 |
| 30 sec. | 1.71 | " | 0.34 |
| 45 sec. | 1.80 | " | 0.18 |
| 60 sec. | 1.87 | " | 0.11 |
| 90 sec. | 1.89 | " | 0.06 |
| 2 min. | 1.90 | " | 0.05 |
| 3 min. | 1.90 | " | 0.05 |
| 4 min. | 1.90 | " | 0.05 |

¹Detectability limit for $Fe^{+++}$ $Cu^{++}$ is readily recovered from the aqueous strip solution in a purity of 99+% by electrolysis.

EXAMPLE C

The process Procedure 1 was essentially followed for $Cu^{++}$ and $Zn^{++}$ extractions except that the 8-(decylethylbenzenesulfonamido)quinoline of Example III was used as 5, 10 and 15% wt./vol. solutions in aliphatic kerosene (Kermac 470B), and such solutions were contacted with the aqueous metal containing solutions two times for 15-20 minutes each time to ensure maximum loading. Results are set forth in the following Table C:

Table C

| Metal | Reagent Concentration | Loaded Organic g./l. Metal |
|---|---|---|
| $Cu^{++}$ | 5 | 2.83 |
| " | 10 | 5.41 |
| " | 15 | 8.25 |
| $Zn^{++}$ | 5 | 2.82 |
| " | 10 | 5.90 |
| " | 15 | 8.30 |

The 15% zinc loaded organic was washed once at an organic:aqueous phase ratio of 1:1 for 15 minutes with 1M $(NH_4)_2SO_4$. The pH of the aqueous wash went from 5.7 to 8.1 and it had a $Zn^{++}$ content of 0.193 g./l. The organic phase was then contacted with 100 g./l. $H_2SO_4$ to strip the zinc. The stripped organic had a $Zn^{++}$ content of <0.0005 g./l. and the aqueous strip solution had an $NH_3$ content of 0.026 M.

A corresponding 8-(decylethylbenzenesulfonamido)-quinoline prepared ultimately from a decylethylbenzene wherein the alkylation had been carried out at 0°-5° C. (see Table I) yielded a $Cu^{++}$ complex which caused gelling when aliphatic kerosene (Kermac 470B) was used but which was readily soluble in Aromatic 150 kerosene.

EXAMPLE D

Example C was essentially repeated except using the sulfonamidoquinoline of Example IV. The resulting $Cu^{++}$ complexes caused the kerosene solution to gel. The $Zn^{++}$ complexes produced a hazy organic but the same analyzed 3.40 and 7.05 g./l. $Zn^{++}$ at 5 and 10% wt./vol. concentrations, respectively. The reagent and its $Cu^{++}$ complex were soluble in Aromatic 150 kerosene and the Procedure 1 process yielded a separated organic which analyzed 3.06 g./l. $Cu^{++}$ with no precipitation.

EXAMPLE E

Example C was partially repeated except using the 8-(octylmethylbenzenesulfonamido)quinoline of Example V. At 15% wt./vol. in Aromatic 150, the reagent maximum loaded 9.80 g./l. $Cu^{++}$ and 10.3 g./l. $Zn^{++}$. In Kermac 470B kerosene, pills were formed during the extractions indicating partial insolubility of the metal complexes.

EXAMPLE F

The process Procedure 1 was used with the 8-(nonylmethylbenzenesulfonamido)quinoline of Example VI in Aromatic 150. Results were as follows:

Table F-1

| Metal | Organic g./l. Metal* |
|---|---|
| $Cu^{++}$ | 2.08 |
| $Ni^{++}$ | 1.86 |
| $Co^{++}$ | 1.76 |
| $Co^{+++}$ | 0.00325 |
| $Zn^{++}$ | 2.09 |

*Some emulsion problems were encountered thus the samples were centrifuged prior to the analysis of the organic phases.

EXAMPLE G

A 10% wt./vol. solution of the 8-(decylisopropylbenzenesulfonamido)quinoline of Example VII in aliphatic kerosene (Kermac 470B) was maximum loaded as in Example C with $Cu^{++}$. The organic phase analyzed 6.25 g./l. $Cu^{++}$. The process Procedure 2 was also followed using a 0.1M solution of the sulfonamidoquinoline in the aliphatic kerosene. The 0.2M $CuSO_4$ aqueous solution was mixed with pH adjusting solutions as indicated in the following Table:

Table G-1

| pH Adjusting Solution | Aqueous Raffinate pH | Organic g./l. $Cu^{++}$ |
|---|---|---|
| 0.5M $H_2SO_4$ | 0.47 | 0.411 |
| 0.1M $H_2SO_4$ | 1.02 | 1.48 |
| 0.05M NaOH | 1.61 | 2.27 |

EXAMPLE H

The process of Procedure 1 was carried out with the 8-(diamylbenzenesulfonamido)quinoline of Example VIII dissolved in Aromatic 150. Results are set forth in the following Table H-1:

Table H-1

| Metal | Organic g./l. Metal |
|---|---|
| $Cu^{++}$ | 2.90[1] |
| $Ni^{++}$ | 2.47 |
| $Co^{+++}$ | 0.0090 |
| $Co^{++}$ | 1.74 |
| $Zn^{++}$ | 3.31 |

[1]When a 5.0% wt./vol. solution of the sulfonamidoquinoline in Aromatic 150 was contacted twice with the $Cu^{++}$ aqueous solution, the organic analyzed 3.62 g./l. $Cu^{++}$ but some precipitation was evident. Precipitation was also evident when Kermac 470B was substituted for Aromatic 150. When benzene was used as the solvent in the Procedure 1 process with one contact with the $Cu^{++}$ solution, the separated organic analyzed 2.99 g./l. $Cu^{++}$ with no precipitation.

The Procedure 2 process was also followed using the Aromatic 150 solution with the 0.2M $CuSO_4$ aqueous solution being mixed with pH adjusting solutions as indicated in the following Table H-2:

Table H-2

| pH Adjusting Solution | Aqueous Raffinate pH | Organic g./l. $Cu^{++}$ |
|---|---|---|
| 0.5M $H_2SO_4$ | 0.49 | 0.148 |
| 0.1M $H_2SO_4$ | 1.08 | 0.930 |
| 0.05M NaOH | 1.71 | 1.99 |

EXAMPLE J

Process Procedure 1 was used with a 0.1M solution of the 8-(sec-amylbenzenesulfonamido)quinoline of Example IX in benzene and the $Cu^{++}$ containing aqueous solution. The resulting organic phase analyzed 3.58 g./l. $Cu^{++}$. In repeating Procedure 1 with a corresponding solution of the sulfonamidoquinoline of Example IX in Aromatic 150, precipitates formed with $Cu^{++}$ and also with $Ni^{++}$ (the filtered organics analyzed 1.01 g./l. $Cu^{++}$ and 0.396 g./l. $Ni^{++}$, respectively) and an emulsion formed with $Zn^{++}$ (the organic analyzed 0.367 g./l. $Zn^{++}$). $Co^{++}$ did not form a precipitate and the organic analyzed 1.70 g./l. $Co^{++}$.

In comparison to the data of Examples H and J, an attempt was made to extract $Cu^{++}$ in accordance with Procedure 1 with a 0.1M solution of 8-(2,5-dimethylbenzenesulfonamido)quinoline in benzene. After contact for 1 hour, a granular precipitate adhered to the sides of the sample bottle and phase separation was slow. The aqueous was pipetted off and the organic phase was again contacted with fresh $Cu^{++}$ aqueous solution. After setting overnight, most of the resulting $Cu^{++}$ complex had settled out. When Aromatic 150 was substituted for the benzene, the 8-(2,5-dimethylbenzenesulfonamido)quinoline dissolved with heating and initially remained in solution after cooling but crystals formed overnight. Prior to crystal formation, an attempt was made to maximum load the solution with $Cu^{++}$ (2 contacts with the $Cu^{++}$ aqueous solution of Procedure 1). Precipitate formed and was filtered off and the organic analyzed only 0.0610 g./l. Cu. Similarly, an attempt was made to dissolve 8-(4-methylbenzenesulfonamido)quinoline at a level of 0.1M in Aromatic 150. Even with heating and shaking, not all of the compound went into solution. The excess was filtered off and the resulting solution of unknown concentration (less than 0.1M) was used in the Procedure 1 process. Emulsions and precipitates formed in all cases with $Cu^{++}$, $Ni^{++}$, $Co^{++}$, $Zn^{++}$. The respective organics after centrifuging analyzed 0.0985 g./l. $Cu^{++}$, 0.0215 g./l. $Ni^{++}$, 0.130 g./l. $Co^{++}$ and 0.025 g./l. $Zn^{++}$. When an attempt was made to dissolve the 8-(4-methylbenzenesulfonamido)quinoline in benzene at a concentration of 0.1 molar, heating was required and some of the compound crystallized out after cooling overnight. The resulting organic was contacted with a $Cu^{++}$ containing solution in accordance with Procedure 1. The separated organic analyzed only 0.22 g./l. $Cu^{++}$.

EXAMPLE K

The Procedure 1 process was carried out with the 8-(dinonylnaphthalenesulfonamido)quinoline of Example X dissolved in Kermac 470B kerosene at the 0.1M level. Results are as follows:

Table K-1

| Metal | Organic g./l. Metal |
|---|---|
| $Cu^{++}$ | 2.19 |
| $Ni^{++}$ | 1.91 |
| $Co^{++}$ | 1.35 |
| $Co^{+++}$ | 0.0710 |
| $Zn^{++}$ | 2.20 |

The process of Procedure 2 was also followed using a 0.15 molar aliphatic kerosene (Kermac 470B) solution of the reagent of Example X with the 0.2M $CuSO_4$ aqueous solution being mixed with pH adjusting solutions as indicated in the following Table K-2:

Table K-2

| pH Adjusting Solution | Aqueous Raffinate pH | Organic g./l. $Cu^{++}$ |
|---|---|---|
| 0.5M $H_2SO_4$ | 0.6 | 1.19 |
| 0.25 M $H_2SO_4$ | 0.7 | 1.32 |
| 0.1M $H_2SO_4$ | 1.1 | 1.70 |
| $H_2O$ | 1.3 | 2.40 |
| 0.005M NaOH | 1.4 | 2.62 |

EXAMPLE L

Process Procedure 1 was used with a 0.1M solution of the 8-(heptylbenzenesulfonamido)quinoline of Example XI in benzene and the $Cu^{++}$ containing aqueous solution. The resulting organic phase analyzed 3.28 g./l. $Cu^{++}$ with some slight precipitation evident which might be attributed to trace impurities. When this was repeated with a 0.1M solution of the sulfonamidoquinoline of Example XI in Aromatic 150 (two contacts with the $Cu^{++}$ containing aqueous solution) some granular precipitate settled out of the organic upon standing overnight and the organic analyzed 1.66 g./l. $Cu^{++}$.

EXAMPLE M

Procedure 1 was followed with the 8-(pentadecylbenzenesulfonamido)quinoline of Example XII dissolved in Aromatic 150. Results were as follows:

Table M-1

| Metal | Organic g./l. Metal |
|---|---|
| $Cu^{++}$ | 3.26 |
| $Ni^{++}$ | 2.83 |
| $Co^{++}$ | 1.84 |
| $Co^{+++}$ | 0.0053 |
| $Zn^{++}$ | 3.25 |

In other tests according to Procedure 1 with the $Cu^{++}$ aqueous solution, a precipitate formed when the reagent of Example XII was dissolved in Kermac 470B kerosene at 5% wt./vol. However, when 10% wt./vol. solutions in either 50:50 or 75:25 volume mixtures of Kermac 470B and Aromatic 150 were used, no precipitates formed and the organic and aqueous phases showed a clean break after the extraction-contacting period.

As in previous Examples, the process of Procedure 2 was followed with a 0.1M solution of the 8-(pentadecylbenzenesulfonamido)quinoline in Aromatic 150 and results are set forth in the following Table:

Table M-2

| pH Adjusting Solution | Aqueous Raffinate pH | Organic g./l. $Cu^{++}$ |
|---|---|---|
| 0.5M $H_2SO_4$ | 0.50 | 0.745 |
| 0.1M $H_2SO_4$ | 0.99 | 2.03 |
| 0.05M NaOH | 1.49 | 2.75 |

EXAMPLE N

The 8-(n-hexadecylbenzenesulfonamido)quinoline of Example XIII was dissolved in benzene at a level of 0.1M and contacted with the $Cu^{++}$ containing solution in accordance with process Procedure 1. The separated organic analyzed 2.10 g./l. $Cu^{++}$ and there was some precipitation (slight to moderate) during the extraction.

EXAMPLE O

The 8-(hexadecylbenzenesulfonamido)quinoline of Example XIV was dissolved in Aromatic 150 at a level of 15% wt./vol. and contacted with the $Cu^{++}$ and $Zn^{++}$ aqueous solutions in accordance with Procedure 1. The resulting organic phases analyzed 10.3 g./l. $Cu^{++}$ and 8.8 g./l. $Zn^{++}$.

EXAMPLE P

The process of Procedure 1 was repeated using the 8-(triisopropylbenzenesulfonamido)quinoline of Example XV in Aromatic 150. Results were as follows:

Table P-1

| Metal | Organic g./l. Metal |
|---|---|
| $Cu^{++}$ | 2.91 |
| $Ni^{++}$ | 2.50 |
| $Co^{++}$ | 1.66 |
| $Co^{+++}$ | 0.0005 |
| $Zn^{++}$ | 1.28* |

*Some precipitation was evident

EXAMPLE Q

A 5% wt./vol. solution of the 8-(dodecylbenzenesulfonamido)-2-methylquinoline of Example XVI in Aromatic 150 was prepared and used in the Procedure 1 process with the $Cu^{++}$ and $Zn^{++}$ aqueous solutions. The resulting solution of the $Cu^{++}$ complex analyzed 3.03 g./l. $Cu^{++}$ and was an iridescent blue-green color (a slight precipitate was removed by filtration). A ball of precipitate formed during the zinc extraction and dissolved upon the addition of an equal part of benzene. The reagent per se was not soluble in Kermac 470B.

EXAMPLE R

The process of Procedure 1 was used with the 8-(decylmethylbenzenesulfonamido)-2-methylquinoline of Example XVII in both Kermac 470B and Aromatic 150. Results as follows:

Table R-1

| Solvent and Metal | Organic g./l. Metal |
|---|---|
| Kermac 470B | |
| $Cu^{++}$ | 2.88 |
| $Ni^{++}$ | 0.273 |
| $Co^{++}$ | 0.477 |
| $Co^{+++}$ | <0.0005 |
| $Zn^{++}$ | 0.518 |
| Aromatic 150 | |
| $Cu^{++}$ | 2.21 |
| $Ni^{++}$ | 1.69 |
| $Co^{+++}$ | 0.0006 |
| $Zn^{++}$ | 2.32 |

The Procedure 2 process was followed with the Aromatic 150 solution of the 8-(decylmethylbenzenesulfonamido)-2-methylquinoline as in previous Examples:

Table R-2

| pH Adjusting Solution | Aqueous Raffinate pH | Organic g./l. $Cu^{++}$ |
|---|---|---|
| 0.5M $H_2SO_4$ | 0.63 | <0.0005 |
| 0.2M $H_2SO_4$ | 1.33 | 0.0019 |
| 0.1M $H_2SO_4$ | 1.65 | 0.0068 |
| $H_2O$ | 2.54 | 0.226 |
| 0.05M NaOH | 2.89 | 0.930 |
| 0.1M NaOH | 3.37 | 1.52 |

Procedure 4 processing was also followed with the Aromatic 150 solution as follows (raffinate $NH_3$ content was not determined):

Table R-3

| | Loaded Organic From Step 2 — 3.14 g./l. $Cu^{++}$ | |
|---|---|---|
| Strip Solution g./l. $H_2SO_4$ | Stripped Organic g./l. $Cu^{++}$ | Wash Solution pH |
| 100 | 1.08 | 3.84 |
| 150 | 1.45 | 5.45 |
| 200 | 1.20 | 3.99 |
| 250 | 0.378 | 3.84 |

The Procedure 3 process using the Aromatic 150 solution of 8-(decylmethylbenzenesulfonamido)-2-methylquinoline was followed in respect of $Cu^{++}$ and $Zn^{++}$ and results are set forth in the following Table:

Table R-4

| Metal | Metal Concentration In Organic g./l. |
|---|---|
| $Cu^{++}$ | 0.315 |
| " | 0.300 |
| " | 0.149 |
| " | 0.0416 |
| $Cu^{++}$ | 0.0114 |
| " | 0.0045 |
| $Zn^{++}$ | 0.351 |
| " | 0.342 |
| " | 0.322 |
| " | 0.218 |
| " | 0.115 |
| " | 0.0535 |

EXAMPLE S

The 8-(decylmethylbenzenesulfonamido)-6-methylquinoline of Example XVIII was dissolved at a concentration of 0.1M in Aromatic 150 and used in accordance with the processes of Procedures 1–4 with results as reported in the following Tables.

Table S-1

| | Procedure 1 |
|---|---|
| Metal | Organic g./l. Metal |
| $Cu^{++}$ | 3.08 |
| $Ni^{++}$ | 2.63 |
| $Co^{++}$ | 1.80 |
| $Co^{+++}$ | 0.0007 |
| $Zn^{++}$ | 2.98 |

Table S-2

| | Procedure 2 | |
|---|---|---|
| pH Adjusting Solution | Aqueous Raffinate pH | Organic g./l. $Cu^{++}$ |
| 0.5M $H_2SO_4$ | 0.61 | 0.232 |
| 0.2M $H_2SO_4$ | 1.20 | 1.05 |
| 0.1M $H_2SO_4$ | 1.40 | 1.28 |
| $H_2O$ | 1.59 | 1.89 |
| 0.05M NaOH | 1.74 | 2.29 |
| 0.1M NaOH | 1.93 | 2.54 |

Table S-3

| | Procedure 3 |
|---|---|
| Metal | Organic g./l. Metal |
| $Cu^{++}$ | 0.320 |
| " | 0.316 |
| " | 0.329 |
| " | 0.319 |
| " | 0.336 |
| " | 0.325 |
| $Zn^{++}$ | 0.355 |
| " | 0.349 |
| " | 0.339 |
| " | 0.348 |
| " | 0.248 |
| " | 0.240 |

Table S-4

| | Procedure 4 | |
|---|---|---|
| | Loaded Organic From Step 2 — 3.16 g./l. $Zn^{++}$ | |
| Strip Solution g./l. $H_2SO_4$ | Stripped Organic g./l. $Zn^{++}$ | Aqueous Raffinate $NH_3$-M |
| 25 | 0.0051 | 0.018 |
| 50 | 0.0035 | 0.020 |
| 75 | 0.0030 | 0.020 |
| 100 | <0.0005 | 0.022 |
| 150 | 0.0020 | 0.021 |

EXAMPLE T

As in Example S, a 0.1M solution of the 8-(decylmethylbenzenesulfonamido)-6-methoxyquinoline of Example XIX in Aromatic 150 was prepared and used in accordance with the processes of Procedures 1, 2 and 4 with the results being reported in the following Tables:

Table T-1

| | Procedure 1 |
|---|---|
| Metal | Organic g./l. Metal |
| $Cu^{++}$ | 3.30 |
| $Ni^{++}$ | 2.32 |
| $Co^{++}$ | 1.42 |
| $Co^{+++}$ | 0.0019 |
| $Zn^{++}$ | 3.14 |

Table T-2

| | Procedure 2 | |
|---|---|---|
| pH Adjusting Solution | Aqueous Raffinate pH | Organic g./l. $Cu^{++}$ |
| 0.5M $H_2SO_4$ | 0.54 | 0.220 |
| 0.2M $H_2SO_4$ | 1.01 | 0.765 |
| 0.1M $H_2SO_4$ | 1.25 | 1.05 |
| $H_2O$ | 1.59 | 1.36 |
| 0.005M NaOH | 1.60 | 1.57 |

Table T-3

| | Procedure 4 |
|---|---|
| | Loaded Organic From Step 2 — 3.24 g./l. $Cu^{++}$ |
| Strip Solution g./l. $H_2SO_4$ | Stripped Organic g./l. $Cu^{++}$ |
| 100 | 1.05 |
| 150 | 0.358 |
| 250 | 0.0395* |

*The stripped organic was washed with water. The pH of the water before the wash step was 5.7 and after was 4.6.

EXAMPLE U

The process of Procedure 1 was followed using the 8-(decylmethylbenzenesulfonamido)-5-nitroquinoline of Example XX dissolved at a concentration of 0.1M in Aromatic 150 and also in benzene. Results are set forth in Table U-1 which follows:

Table U-1

| Solvent and Metal | Organic g./l. Metal |
|---|---|
| Aromatic 150 | |
| $Cu^{++}$ | 2.58 |
| $Zn^{++}$ | 2.56 |
| Benzene | |
| $Cu^{++}$ | 2.73 |
| $Zn^{++}$ | 2.72 |

Likewise in the Procedure 2 process with the Aromatic 150 solution, the results were as follows:

Table U-2

| pH Adjusting Solution | Aqueous Raffinate pH | Organic g./l. $Cu^{++}$ |
|---|---|---|
| 0.5M $H_2SO_4$ | 0.60 | 0.147 |
| 0.2M $H_2SO_4$ | 1.13 | 0.391 |
| 0.1M $H_2SO_4$ | 1.39 | 0.530 |
| $H_2O$ | 1.83 | 0.945 |
| 0.05M NaOH | 1.82 | 1.05 |

When the Aromatic 150 solution was maximum loaded with $Cu^{++}$ (2.80 g./l.) and stripped, 250 g./l. aqueous $H_2SO_4$ yielded a stripped organic with a $Cu^{++}$ content of 0.0550 g./l. and 150 g./l. aqueous $H_2SO_4$ yielded a stripped organic with a $Cu^{++}$ content of 0.523 g./l.

EXAMPLE W

Process Procedures 1 and 2 were employed with a 0.1M Aromatic 150 solution of the 8-(decylmethylbenzenesulfonamido)-5,7-dichloroquinoline of Example XXI. Results were as follows:

Table W-1

| | Procedure 1 |
|---|---|
| Metal | Organic g./l. Metal |
| $Cu^{++}$ | 2.62 |
| $Ni^{++}$ | 2.19 |
| $Zn^{++}$ | 2.15 |

Table W-2

| | Procedure 2 | |
|---|---|---|
| pH Adjusting Solution | Aqueous Raffinate pH | Organic g./l. $Cu^{++}$ |
| 0.5M $H_2SO_4$ | 0.54 | <0.0005 |
| 0.2M $H_2SO_4$ | 1.10 | 0.0067 |
| 0.1M $H_2SO_4$ | 1.49 | 0.0204 |
| $H_2O$ | 2.37 | 0.253 |
| 0.05M NaOH | 2.50 | 0.316 |

The reagent of Example XXI maximum loaded 2.74 g./l. $Cu^{++}$ using the aqueous $Cu^{++}$ solution of Procedure 1. The data of Table W-2 shows that this reagent extracts $Cu^{++}$ at a higher pH than the new compound of Example II which does not have chloro substituents.

EXAMPLE Y

Example W was essentially repeated except using the 8-(dodecylphenylmethanesulfonamido)quinoline of Example XXII. Results were as follows:

Table Y-1

| | Procedure 1 |
|---|---|
| Metal | Organic g./l. Metal |
| $Cu^{++}$ | 2.61 |
| $Ni^{++}$ | 2.10 |
| $Zn^{++}$ | 2.60 |

Table Y-2

| | Procedure 2 | |
|---|---|---|
| pH Adjusting Solution | Aqueous Raffinate pH | Organic g./l. $Cu^{++}$ |
| 0.5M $H_2SO_4$ | 0.57 | 0.130 |
| 0.1M $H_2SO_4$ | 1.31 | 1.15 |
| 0.05M $H_2SO_4$ | 1.36 | 1.24 |
| $H_2O$ | 1.55 | 1.59 |
| 0.05M NaOH | 1.83 | 1.95 |
| 0.1M NaOH | 2.13 | 2.21 |

When dissolved at a 0.1M concentration in Kermac 470B and contacted with the aqueous $Cu^{++}$ solution of Procedure 1, the compound of Example XXII yielded an amber colored emulsion which gelled upon setting.

EXAMPLE Z

The Procedure 1 process was used with a 0.1M Aromatic 150 solution of the 8-(n-hexadecanesulfonamido)quinoline of Example XXIII. Table Z-1 gives the results:

Table Z-1

| Metal | Organic g./l. Metal |
|---|---|
| $Cu^{++}$ | 3.07 |
| $Ni^{++}$ | 2.65 |
| $Co^{++}$ | 1.76* |
| $Zn^{++}$ | —** |

*Some precipitate
**Precipitate thus organic not analyzed

When process Procedure 1 was repeated with the $Cu^{++}$ containing aqueous solution and a 0.1M solution of the 8-(n-hexadecanesulfonamido)quinoline in benzene, the separated organic analyzed 1.59 g./l. and some precipitation was evident.

EXAMPLE AA

Procedures 1, 2 and 4 were used with a 0.1M solution of the 8-(2-ethylhexanesulfonamido)quinoline of Example XXIV in Aromatic 150. Results are set forth in the following Tables:

Table AA-1

| | Procedure 1 |
|---|---|
| Metal | Organic g./l. Metal |
| $Cu^{++}$ | 2.85 |
| $Ni^{++}$ | 2.42 |
| $Zn^{++}$ | 2.80 |

Table AA-2

| | Procedure 2 | |
|---|---|---|
| pH Adjusting Solution | Aqueous Raffinate pH | Organic g./l. $Cu^{++}$ |
| 0.5M $H_2SO_4$ | 0.74 | 0.164 |
| 0.2M $H_2SO_4$ | 1.16 | 0.930 |
| 0.1M $H_2SO_4$ | 1.32 | 1.27 |
| $H_2O$ | 1.55 | 1.72 |
| 0.05M NaOH | 1.75 | 2.00 |

Table AA-3

| Procedure 4 | | |
|---|---|---|
| Loaded Organic* From Step 2 — about 2.80 g./l. $Cu^{++}$ | | |
| Strip Solution g./l. $H_2SO_4$ | Stripped Organic g./l. $Cu^{++}$ | Wash Solution pH |
| 100 | 0.100 | 5.36 |
| 150 | 0.0025 | 5.36 |
| 200 | 0.0025 | 3.93 |
| 250 | — | 4.8 |

*The starting loaded organic was not analyzed, thus $Cu^{++}$ content was estimated.

EXAMPLE BB

A 0.1M solution of the 8-(n-octanesulfonamido)quinoline of Example XXVII in Aromatic 150 was contacted two times at an organic:aqueous phase ratio of 1:1 for 1 hour each time with the $Cu^{++}$ aqueous solution of Procedure 1. The maximum loaded organic analyzed 2.20 g./l. $Cu^{++}$. There was no evidence of precipitation.

EXAMPLE CC

Process Procedure 1 was used with a 0.1M solution of the 8-(n-pentanesulfonamido)quinoline of Example XXVIII in benzene and the $Cu^{++}$ containing aqueous solution. The separated organic analyzed 3.44 g./l. $Cu^{++}$. However, when an attempt was made to maximum load a 0.1M solution of the 8-(n-pentylsulfonamido)quinoline in Aromatic 150 as in Example BB, a moderate amount of precipitate fell out of solution and was filtered off. The filtered organic analyzed 0.860 g./l. $Cu^{++}$.

EXAMPLE DD

Procedures 1–4 were also used with the 8-(isodecanesulfonamido)quinoline of Example XXV. These results are as follows (0.1M solution in Aromatic 150):

Table DD-1

| Metal | Procedure 1 Organic g./l. Metal |
|---|---|
| $Cu^{++}$ | 2.80 |
| $Ni^{++}$ | 2.50 |
| $Co^{++}$ | 1.80 |
| $Co^{+++}$ | 0.0006 |
| $Zn^{++}$ | 2.70 |

Table DD-2

| pH Adjusting Solution | Procedure 2 Aqueous Raffinate pH | Organic g./l. $Cu^{++}$ |
|---|---|---|
| 0.5M $H_2SO_4$ | 0.49 | 0.206 |
| 0.2M $H_2SO_4$ | 1.06 | 1.14 |
| 0.1M $H_2SO_4$ | 1.23 | 1.50 |
| $H_2O$ | 1.61 | 2.25 |
| 0.05M NaOH | 1.62 | 2.13 |
| 0.1M NaOH | 1.87 | 2.39 |

Table DD-3

| Metal | Procedure 3 Organic g./l. Metal |
|---|---|
| $Cu^{++}$ | 0.306 |
| " | 0.312 |
| " | 0.318 |
| " | 0.316 |
| " | 0.317 |
| " | 0.314 |
| $Zn^{++}$ | 0.356 |
| " | 0.356 |
| " | 0.340 |
| " | 0.275 |
| " | 0.230 |
| " | 0.171 |

Table DD-4

| Procedure 4 | | |
|---|---|---|
| Loaded Organic From Step — 2.87 g./l. $Cu^{++}$ | | |
| Strip Solution g./l. $H_2SO_4$ | Stripped Organic g./l. $Cu^{++}$ | Wash Solution pH |
| 75 | 0.0148 | 3.33 |
| 100 | 0.0083 | 3.39 |
| 150 | 0.0029 | 5.85 |
| 200 | 0.0271 | 4.52 |
| Loaded Organic From Step 2 — 2.95 g./l. $Zn^{++}$ | | |
| Strip Solution g./l. $H_2SO_4$ | Stripped Organic g./l. $Zn^{++}$ | Aqueous Raffinate $NH_3$-M |
| 25 | 0.0012 | 0.018 |
| 50 | <0.0005 | 0.020 |
| 75 | <0.0005 | 0.019 |
| 100 | <0.0005 | 0.020 |
| 150 | <0.0005 | 0.020 |

EXAMPLE EE

An 8% wt./vol. solution of the 8-($C_{14}$–$C_{16}$-alkenylsulfonamido)quinoline of Example XXVI in Kermac 470B kerosene was contacted in accordance with the Procedure 1 process. The resulting organic analyzed 3.66 g./l. $Cu^{++}$.

EXAMPLE FF

A 0.05M $Ag^+$ solution was prepared by dissolving 0.84 g. $AgNO_3$ and 13.2 g. $(NH_4)_2SO_4$ in 20 ml. of 2.0M $NH_4OH$ and diluting to 100 ml. with water. A 0.1M solution of the 8-(decylmethylbenzenesulfonamido)-quinoline of Example II in Aromatic 150 was then contacted at a 1:1 organic:aqueous phase ratio with the $Ag^+$ solution for one hour with shaking. After separation of the phases, the organic analyzed 2.96 g./l. $Ag^+$. Portions of the loaded organic phase were then contacted with shaking for 1 hour with equal volumes of various aqueous solutions to strip the $Ag^+$ therefrom. Results were as follows:

Table FF-1

| Aqueous Strip Solution | Stripped Organic g./l. $Ag^+$ |
|---|---|
| 150 g./l. $H_2SO_4$ | <0.01 |
| 1.0M $HNO_3$ | <0.01 |
| 1.0M HCl | 0.04 |

EXAMPLE GG

Example FF was repeated except that the starting aqueous solution was prepared by attempting to dissolve 1.71 g. Hg $(NO_3)_2$ in 100 ml. water. Almost all of the $Hg(NO_3)_2$ dissolved with residual precipitate being filtered off to yield a solution which was close to 0.05M in $Hg^{++}$ (pH 2.02). The separated loaded organic analyzed 10.5 g./l. $Hg^{++}$. When stripped with an equal volume of 1.0M HCl, the organic analyzed 0.93 g./l.

EXAMPLE HH

A 5.5% wt./vol. solution of the 8-(decylmethylbenzenesulfonamido)quinoline of Example II in Kermac 470B kerosene was contacted with stirring at an organic:aqueous phase ratio of 1:4 with an aqueous solution containing 2.5 g./l. $Pb^{++}$ from $Pb(NO_3)_2$ in water (pH adjusted to 7.1 during extraction). The contact time was 2.0 minutes. The separated organic analyzed 9.56 g./l. $Pb^{++}$. The loaded organic was stripped with an aqueous $HNO_3$ (150 g./l.) at an organic:aqueous phase ratio of 6:1 to yield a barren stripped organic. Some precipitation of $Pb(NO_3)_2$ was noted in the aqueous strip solution.

The above Examples show metal recovery from various starting aqueous solutions. It is clear that the metal content of such starting solutions is not critical and can vary widely, it being only necessary that the process extracts at least a portion of the metal values therefrom. In preferred aspects, the metal content will range from 0.1 to 80 g./l. of the respective metals being extracted.

The embodiments of the invention in which an exclusive property or privilege is claimed are defined as follows:

1. Compounds of the structure:

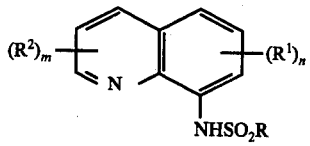

where R is selected from the group consisting of alkyl and alkenyl of 8 to 20 carbon atoms and

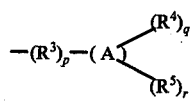

where $R^3$ is an alkylene of 1 to about 20 carbon atoms, $p$ is 0 or 1, A is a monocyclic hydrocarbon ring or a bicyclic hydrocarbon ring wherein the ring or rings are 5 or 6 membered, $q$ is a whole integer selected from 1, 2 and 3, $r$ is 0 or 1, and $q + r = 1$ to 3, $R^4$ is an alkyl or alkenyl of up to about 20 carbon atoms such that the total number of carbon atoms in $(R^4)_q$ is at least 8 with the proviso that when $q$ is 2 at least one $R^4$ contains 5 or more carbon atoms and when $q$ is 2 or 3 and more than one of the $R^4$ groups are branched chain the branched chain groups are not on adjacent carbon atoms, $R^5$ is —Cl, —Br, —NO$_2$ or —O—$R^6$ wherein $R^6$ is a hydrocarbon group radical of from 1 to about 20 carbon atoms, $n$ is 0, 1 or 2 with the proviso that when $n$ is 2 the $R^1$ substituents are not on adjacent carbon atoms, $m$ is 0 or 1 and $R^1$ and $R^2$ are selected from the group consisting of hydrocarbon groups of from 1 to 5 carbon atoms, —Cl, —Br, NO$_2$ and —O—$R^6$, said compounds being further characterized as having solubilities of at least 2% by weight in an essentially water-immiscible, liquid hydrocarbon solvent having a flash point of at least 150° F and also further characterized in that the Cu++ complexes thereof have solubilities of at least 2% by weight in the said solvent.

2. The compounds of claim 1 wherein R is an alkyl radical of 8 to about 20 carbon atoms.

3. The compounds of claim 2 wherein R is straight chained.

4. The compounds of claim 3 wherein R is n-octyl.

5. The compounds of claim 3 wherein R is n-hexadecyl.

6. The compounds of claim 2 wherein R is branched chain.

7. The compounds of claim 6 wherein R is 2-ethylhexyl.

8. The compounds of claim 6 wherein R is isodecyl.

9. The compounds of claim 2 wherein $m$ and $n$ are 0.

10. The compounds of claim 1 wherein R is an alkenyl radical of 8 to about 20 carbon atoms.

11. The compounds of claim 10 wherein $m$ and $n$ are 0.

12. The compounds of claim 1 wherein R is

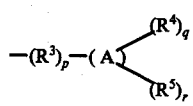

13. The compounds of claim 12 wherein $p$ is 1.

14. The compounds of claim 13 wherein $R^3$ is an alkylene radical of 1 or 2 carbon atoms.

15. The compounds of claim 14 wherein the ring or rings in A are 6-membered.

16. The compounds of claim 15 wherein A is phenyl.

17. The compounds of claim 16 wherein $R^4$ is an alkyl radical.

18. The compounds of claim 17 wherein one $R^4$ radical contains at least 8 carbon atoms.

19. The compounds of claim 18 wherein the $R^4$ radical containing at least 8 carbon atoms is branched chain.

20. The compounds of claim 19 wherein the branched chain alkyl radical is a linear alkylate group.

21. The compounds of claim 20 wherein $R^3$ is methylene, $q$ is 1, $r$ is 0 and $R^4$ is dodecyl.

22. The compounds of claim 13 wherein $m$ and $n$ are 0.

23. The compounds of claim 12 wherein $p$ is 0.

24. The compounds of claim 23 wherein $r$ is 0.

25. The compounds of claim 23 wherein the ring or rings in A are 6-membered.

26. The compounds of claim 25 wherein A is naphthyl.

27. The compounds of claim 25 wherein A is phenyl.

28. The compounds of claim 23 wherein $q$ is 1 and A is phenyl.

29. The compounds of claim 28 wherein $R^4$ is straight chained.

30. The compounds of claim 29 wherein $R^4$ is n-hexadecyl.

31. The compounds of claim 29 wherein $r$ is 0.

32. The compounds of claim 29 wherein $m$ and $n$ are 0.

33. The compounds of claim 28 wherein $R^4$ is branched chain.

34. The compounds of claim 33 wherein $R^4$ is dodecyl.

35. The compounds of claim 33 wherein $R^4$ is pentadecyl.

36. The compounds of claim 33 wherein the branched chain $R^4$ group is a linear alkyl group.

37. The compounds of claim 36 wherein $R^4$ is heptyl.

38. The compounds of claim 36 wherein $R^4$ is dodecyl.

39. The compounds of claim 36 wherein $R^4$ is hexadecyl.

40. The compounds of claim 33 wherein $m$, $n$ and $r$ are 0.

41. The compounds of claim 36 wherein $m$, $n$ and $r$ are 0.

42. The compounds of claim 36 wherein $m$ is 1 and $n$ and $r$ are 0.

43. The compounds of claim 42 wherein $R^2$ is an alkyl group.

44. The compounds of claim 23 wherein $q$ is 2 and A is phenyl.

45. The compounds of claim 44 wherein one of the $R^4$ groups contains 5 carbon atoms and the second $R^4$ group contains at least 5 carbon atoms.

46. The compounds of claim 44 wherein one of the $R^4$ groups contains at least 8 carbon atoms.

47. The compounds of claim 46 wherein the $R^4$ group containing at least 8 carbon atoms is branched chain.

48. The compounds of claim 47 wherein the second $R^4$ group is methyl.

49. The compounds of claim 47 wherein the second $R^4$ group is ethyl.

50. The compounds of claim 47 wherein the second alkyl group is isopropyl.

51. The compounds of claim 48 wherein the branched chain $R^4$ group is nonyl.

52. The compounds of claim 47 wherein the branched chain $R^4$ group is a linear alkylate group.

53. The compounds of claim 52 wherein the branched chain $R^4$ group is octyl and the second $R^4$ radical is methyl.

54. The compounds of claim 52 wherein the branched chain $R^4$ group is decyl and the second $R^4$ radical is methyl.

55. The compounds of claim 52 wherein the branched chain $R^4$ group is decyl and the second $R^4$ group is ethyl.

56. The compounds of claim 52 wherein the banched chain $R^4$ group is decyl and the second $R^4$ group is isopropyl.

57. The compounds of claim 52 wherein the branched chain $R^4$ group is dodecyl and the second $R^4$ group is methyl.

58. The compounds of claim 52 wherein $m$, $n$ and $r$ are 0.

59. The compounds of claim 52 wherein $m$ is 1 and $n$ and $r$ are 0.

60. The compounds of claim 59 wherein $R^2$ is an alkyl group.

61. The compounds of claim 60 wherein $R^2$ is methyl, the branched chain $R^4$ group is decyl and the second $R^4$ group is methyl.

62. The compounds of claim 52 wherein $n$ is 1 and $m$ and $r$ are 0.

63. The compounds of claim 62 wherein the branched chain $R^4$ group is decyl and the second $R^4$ group is methyl.

64. The compounds of claim 63 wherein $R^1$ is nitro.

65. The compounds of claim 63 wherein $R^1$ is methyl.

66. The compounds of claim 63 wherein $R^1$ is $-O-R^6$.

67. The compounds of claim 66 wherein $R^6$ is methyl.

68. The compounds of claim 52 wherein $n$ is 2 and $m$ and $r$ are 0.

69. The compounds of claim 68 wherein $R^1$ is Cl, the branched chain $R^4$ group is decyl and the second $R^4$ group is methyl.

70. The compounds of claim 23 wherein $q$ is 2 and A is naphthyl.

71. The compounds of claim 70 wherein $m$, $n$ and $r$ are 0 and the $R^4$ groups are branched chain.

72. The compounds of claim 71 wherein the $R^4$ groups are nonyl.

73. The compounds of claim 23 wherein $q$ is 3 and A is phenyl.

74. 8-(2-Ethylhexanesulfonamido)quinoline.
75. 8-(n-Octanesulfonamido)quinoline.
76. 8-(n-Hexadecanesulfonamido)quinoline.
77. 8-(Isodecanesulfonamido)quinoline.
78. 8-(Dodecylbenzenesulfonamido)quinoline.
79. 8-(Decylmethylbenzenesulfonamido)quinoline.
80. 8-(Decylethylbenzenesulfonamido)quinoline.
81. 8-(Octylmethylbenzenesulfonamido)quinoline.
82. 8-(Nonylmethylbenzenesulfonamido)quinoline.
83. 8-(Decylisopropylbenzenesulfonamido)quinoline.
84. 8-(Diamylbenzenesulfonamido)quinoline.
85. 8-(Dinonylnaphthalenesulfonamido)quinoline.
86. 8-(Heptylbenzenesulfonamido)quinoline.
87. 8-(Hexadecylbenzenesulfonamdio)quinoline.
88. 8-(2,4,6-Triisopropylbenzenesulfonamido)quinoline.
89. 8-(Dodecylbenzenesulfonamido)-2-methylquinoline.
90. 8-(Decylmethylbenzenesulfonamido)-2-methylquinoline.
91. 8-(Decylmethylbenzenesulfonamido)-6-methylquinoline.
92. 8-(Decylmethylbenzenesulfonamido)-6-methoxyquinoline.
93. 8-(Decylmethylbenzenesulfonamido)-5-nitroquinoline.
94. 8-(Decylmethylbenzenesulfonamido)-5,7-dichloroquinoline.
95. 8-(Dodecylphenylmethanesulfonamido)quinoline.

96. The compounds of claim 1 which are further characterized as having solubilities of at least 2% by weight in a kerosene having a flash point of at least 150° F. and which are still further characterized in that the Cu++ complexes thereof also have solubilities of at least 2% by weight in the said kerosene.

* * * * *

UNITED STATES PATENT AND TRADEMARK OFFICE
CERTIFICATE OF CORRECTION

PATENT NO. : 4,100,163
DATED : July 11, 1978
INVENTOR(S) : VIRNIG, Michael J.

It is certified that error appears in the above-identified patent and that said Letters Patent are hereby corrected as shown below:

Col. 6, line 57, "C-1214L" should read -- C1214 --

Col. 18, line 33, "dinonylnaphthalenesulfonamide" should read

-- dinonylnaphthalenesulfonamido --.

Col. 23, line 37, "50%" should read -- 5.0% --

Col 32, line 25, "0.5 m NaOH" should read -- 0.05 m NaOH --

Col. 33, line 56, "ere" should read -- were --

Claim 1, line 25, "hydrocarbon group radical" should read

-- hydrocarbon group --

Signed and Sealed this

Fourth Day of September 1979

[SEAL]

Attest:

LUTRELLE F. PARKER
Attesting Officer   Acting Commissioner of Patents and Trademarks